US006854467B2

(12) United States Patent
Boekstegers

(10) Patent No.: US 6,854,467 B2
(45) Date of Patent: Feb. 15, 2005

(54) METHODS AND DEVICES FOR DELIVERING A VENTRICULAR STENT

(75) Inventor: Peter Boekstegers, Diessena (DE)

(73) Assignee: Percardia, Inc., Merrimack, NH (US)

(*) Notice: Subject to any disclaimer, the term of this patent is extended or adjusted under 35 U.S.C. 154(b) by 131 days.

(21) Appl. No.: 09/845,154

(22) Filed: May 1, 2001

(65) Prior Publication Data

US 2002/0045928 A1 Apr. 18, 2002

Related U.S. Application Data

(60) Provisional application No. 60/201,732, filed on May 4, 2000.

(51) Int. Cl.[7] .............................................. A61B 19/00
(52) U.S. Cl. .......................... 128/898; 623/1.11; 604/8
(58) Field of Search ................................. 623/902, 903, 623/1.11; 600/16, 37, 585; 604/7, 8, 96.01, 28; 128/898; 606/108, 191–192, 194–195, 198

(56) References Cited

U.S. PATENT DOCUMENTS

| | | | |
|---|---|---|---|
| 3,971,363 A | 7/1976 | Fletcher et al. |
| 4,503,568 A | 3/1985 | Madras |
| 4,733,665 A | 3/1988 | Palmaz |
| 4,769,029 A | 9/1988 | Patel |
| 4,953,553 A | 9/1990 | Tremulis |
| 4,995,857 A | 2/1991 | Arnold |
| 5,035,702 A | 7/1991 | Taheri |
| 5,135,467 A | 8/1992 | Citron |
| 5,190,058 A | 3/1993 | Jones et al. |
| 5,193,546 A | 3/1993 | Shaknovich |
| 5,226,889 A | 7/1993 | Sheiban |
| 5,258,008 A | 11/1993 | Wilk |
| 5,287,861 A | 2/1994 | Wilk |
| 5,292,309 A | 3/1994 | Van Tassel et al. |
| 5,330,486 A | 7/1994 | Wilk |
| 5,344,426 A | 9/1994 | Lau et al. |
| 5,385,541 A | 1/1995 | Kirsch et al. |

(List continued on next page.)

FOREIGN PATENT DOCUMENTS

| | | |
|---|---|---|
| EP | 0 732 088 | 9/1996 |
| EP | 0 792 624 A1 | 9/1997 |
| EP | 0 797 957 A1 | 10/1997 |

(List continued on next page.)

OTHER PUBLICATIONS

US 6,331,185, 12/2001, Gambale et al. (withdrawn)
Tweden et al., "Ventriculocoronary Artery Bypass (VCAB), a Novel Approach to Myocardial Revascularization".
Gardner, M.D. et al., "An Experimental Anatomic Study of Indirect Myocardial Revascularization," *Journal of Surgical research*, May 1971, vol. 11, No. 5, pp 243–247.
Palmaz et al., "Expandable Intrahepatic Portacaval Shunt Stents: Early Experience in the Dog," *AJR*, vol. 145, pp. 821–825.

(List continued on next page.)

*Primary Examiner*—David J. Isabella
*Assistant Examiner*—Urmi Chattopadhyay
(74) *Attorney, Agent, or Firm*—Finnegan, Henderson, Farabow, Garrett & Dunner LLP

(57) ABSTRACT

A method, and related tools for performing the method, of delivering a stent or other like device to the heart to connect the left ventricle to the coronary artery to thereby supply blood directly from the ventricle to the coronary artery may be used to bypass a total or partial occlusion of a coronary artery. The method may include placing a guide device and a dilation device through an anterior wall and a posterior wall of the coronary vessel and through a heart wall between the heart chamber and the coronary vessel. The dilation device may be used to form a passageway in the heart wall at a location defined by the guide device. The method may then include placing a stent within the passageway.

74 Claims, 14 Drawing Sheets

U.S. PATENT DOCUMENTS

| | | |
|---|---|---|
| 5,389,096 A | 2/1995 | Aita et al. |
| 5,409,019 A | 4/1995 | Wilk |
| 5,423,744 A | 6/1995 | Gencheff et al. |
| 5,423,851 A | 6/1995 | Samuels |
| 5,429,144 A | 7/1995 | Wilk |
| 5,443,497 A | 8/1995 | Venbrux |
| 5,456,694 A | 10/1995 | Marin et al. |
| 5,456,712 A | 10/1995 | Maginot |
| 5,456,714 A | 10/1995 | Owen |
| 5,470,320 A | 11/1995 | Tiefenbrun et al. |
| 5,527,337 A | 6/1996 | Stack et al. |
| 5,554,119 A | 9/1996 | Harrison et al. |
| 5,578,075 A | 11/1996 | Dayton |
| 5,593,434 A | 1/1997 | Williams |
| 5,609,626 A | 3/1997 | Quijano et al. |
| 5,611,778 A | 3/1997 | Brinon |
| 5,618,299 A | 4/1997 | Khosravi et al. |
| 5,643,278 A | 7/1997 | Wijay |
| 5,655,548 A | 8/1997 | Nelson et al. |
| 5,662,124 A | 9/1997 | Wilk |
| 5,676,670 A | 10/1997 | Kim |
| 5,733,267 A | 3/1998 | Del Toro |
| 5,755,682 A | 5/1998 | Knudson et al. |
| 5,758,663 A | 6/1998 | Wilk et al. |
| 5,797,920 A | 8/1998 | Kim |
| 5,797,933 A | 8/1998 | Snow et al. |
| 5,807,384 A | 9/1998 | Mueller |
| 5,810,836 A | 9/1998 | Hussein et al. |
| 5,810,871 A | 9/1998 | Tuckey et al. |
| 5,824,038 A | 10/1998 | Wall |
| 5,824,071 A | 10/1998 | Nelson et al. |
| 5,830,222 A | 11/1998 | Makower |
| 5,843,163 A | 12/1998 | Wall |
| 5,851,232 A | 12/1998 | Lois |
| 5,855,597 A | 1/1999 | Jayaraman |
| 5,865,723 A | 2/1999 | Love |
| 5,876,373 A | 3/1999 | Giba et al. |
| 5,876,419 A | 3/1999 | Carpenter et al. |
| 5,878,751 A | 3/1999 | Hussein et al. |
| 5,885,259 A | 3/1999 | Berg |
| 5,893,848 A | 4/1999 | Negus et al. |
| 5,908,028 A | 6/1999 | Wilk |
| 5,908,029 A | 6/1999 | Knudson et al. |
| 5,922,022 A | 7/1999 | Nash et al. |
| 5,925,012 A | 7/1999 | Murphy-Chutorian et al. |
| 5,931,848 A | 8/1999 | Saadat |
| 5,935,119 A | 8/1999 | Guy et al. |
| 5,935,161 A | 8/1999 | Robinson et al. |
| 5,935,162 A | 8/1999 | Dang |
| 5,938,632 A | 8/1999 | Ellis |
| 5,944,019 A | 8/1999 | Knudson et al. |
| 5,961,548 A | 10/1999 | Shmulewitz |
| 5,968,093 A | 10/1999 | Kranz |
| 5,971,993 A | 10/1999 | Hussein et al. |
| 5,976,153 A | 11/1999 | Fischell et al. |
| 5,976,155 A | 11/1999 | Foreman et al. |
| 5,976,159 A | 11/1999 | Bolduc et al. |
| 5,976,169 A | 11/1999 | Imran |
| 5,976,181 A | 11/1999 | Whelan et al. |
| 5,976,182 A | 11/1999 | Cox |
| 5,976,192 A | 11/1999 | McIntyre et al. |
| 5,976,650 A | 11/1999 | Campbell et al. |
| 5,979,455 A | 11/1999 | Maginot |
| 5,980,530 A | 11/1999 | Willard et al. |
| 5,980,533 A | 11/1999 | Holman |
| 5,980,548 A | 11/1999 | Evans et al. |
| 5,980,551 A | 11/1999 | Summers et al. |
| 5,980,552 A | 11/1999 | Pinchasik et al. |
| 5,980,553 A | 11/1999 | Gray et al. |
| 5,980,566 A | 11/1999 | Alt et al. |
| 5,984,955 A | 11/1999 | Wisselink |
| 5,984,956 A | 11/1999 | Tweden et al. |
| 5,984,963 A | 11/1999 | Ryan et al. |
| 5,984,965 A | 11/1999 | Knapp et al. |
| 5,989,207 A | 11/1999 | Hughes |
| 5,989,263 A | 11/1999 | Shmulewitz |
| 5,989,287 A | 11/1999 | Yang et al. |
| 5,993,481 A | 11/1999 | Marcade et al. |
| 5,993,482 A | 11/1999 | Chuter |
| 5,997,525 A | 12/1999 | March et al. |
| 5,997,563 A | 12/1999 | Kretizers |
| 5,997,573 A | 12/1999 | Quijano et al. |
| 5,999,678 A | 12/1999 | Murphy-Chutorian et al. |
| 6,001,123 A | 12/1999 | Lau |
| 6,004,261 A | 12/1999 | Sinofsky et al. |
| 6,004,347 A | 12/1999 | McNamara et al. |
| 6,004,348 A | 12/1999 | Banas et al. |
| 6,007,543 A | 12/1999 | Ellis et al. |
| 6,007,575 A | 12/1999 | Samuels |
| 6,007,576 A | 12/1999 | McClellan |
| 6,010,449 A | 1/2000 | Selmon et al. |
| 6,010,530 A | 1/2000 | Goicoechea |
| 6,017,365 A | 1/2000 | Van Oepen |
| 6,026,814 A | 2/2000 | LaFontaine et al. |
| 6,029,672 A | 2/2000 | Vanney et al. |
| 6,035,856 A | 3/2000 | LaFontaine et al. |
| 6,036,677 A | 3/2000 | Javier, Jr. et al. |
| 6,036,697 A | 3/2000 | DiCaprio |
| 6,039,721 A | 3/2000 | Johnson et al. |
| 6,042,581 A | 3/2000 | Ryan et al. |
| 6,045,565 A | 4/2000 | Ellis et al. |
| 6,053,911 A | 4/2000 | Ryan et al. |
| 6,053,924 A | 4/2000 | Hussein |
| 6,053,942 A | 4/2000 | Eno et al. |
| 6,056,743 A | 5/2000 | Ellis et al. |
| 6,067,988 A | 5/2000 | Mueller |
| 6,068,638 A | 5/2000 | Makower |
| 6,071,292 A | 6/2000 | Makower et al. |
| 6,076,529 A | 6/2000 | Vanney et al. |
| 6,080,163 A | 6/2000 | Hussein et al. |
| 6,080,170 A | 6/2000 | Nash et al. |
| 6,092,526 A | 7/2000 | LaFontaine et al. |
| 6,093,166 A | 7/2000 | Knudson et al. |
| 6,093,177 A | 7/2000 | Javier, Jr. et al. |
| 6,093,185 A | 7/2000 | Ellis et al. |
| 6,095,997 A | 8/2000 | French et al. |
| 6,102,941 A | 8/2000 | Tweden et al. |
| 6,106,538 A | 8/2000 | Shiber |
| 6,110,201 A | 8/2000 | Quijano et al. |
| 6,113,630 A | 9/2000 | Vanney et al. |
| 6,113,823 A | 9/2000 | Eno |
| 6,117,165 A | 9/2000 | Becker |
| 6,120,520 A | 9/2000 | Saadat et al. |
| 6,123,682 A | 9/2000 | Knudson et al. |
| 6,126,649 A | 10/2000 | Van Tassel et al. |
| 6,126,654 A | 10/2000 | Giba et al. |
| 6,132,451 A | 10/2000 | Payne et al. |
| 6,139,541 A | 10/2000 | Vanney et al. |
| 6,152,141 A | 11/2000 | Stevens et al. |
| 6,155,264 A | 12/2000 | Ressemann et al. |
| 6,156,031 A | 12/2000 | Aita et al. |
| 6,157,852 A | 12/2000 | Selmon et al. |
| 6,159,225 A | 12/2000 | Makower |
| 6,162,245 A | 12/2000 | Jayaraman |
| 6,165,185 A | 12/2000 | Shennib et al. |
| 6,165,188 A | 12/2000 | Saadat et al. |
| 6,171,251 B1 | 1/2001 | Mueller et al. |
| 6,171,303 B1 | 1/2001 | Ben-Haim et al. |
| 6,182,668 B1 | 2/2001 | Tweden et al. |
| 6,186,972 B1 | 2/2001 | Nelson et al. |

| | | | | | |
|---|---|---|---|---|---|
| 6,190,353 B1 | 2/2001 | Makower et al. | 6,454,760 B2 | 9/2002 | Vanney |
| 6,193,726 B1 | 2/2001 | Vanney | 6,454,794 B1 | 9/2002 | Knudson et al. |
| D438,618 S | 3/2001 | Solem | 6,458,092 B1 | 10/2002 | Gambale et al. |
| 6,196,230 B1 | 3/2001 | Hall et al. | 6,458,140 B2 | 10/2002 | Akin et al. |
| 6,197,050 B1 | 3/2001 | Eno et al. | 6,458,323 B1 | 10/2002 | Boekstegers |
| 6,197,324 B1 | 3/2001 | Crittenden | 6,464,709 B1 | 10/2002 | Shennib et al. |
| 6,200,310 B1 | 3/2001 | Ben-Haim et al. | 6,475,226 B1 | 11/2002 | Belef et al. |
| 6,200,311 B1 | 3/2001 | Danek et al. | 6,475,244 B2 | 11/2002 | Herweck et al. |
| 6,203,556 B1 | 3/2001 | Evans et al. | 6,482,220 B1 | 11/2002 | Mueller |
| 6,213,126 B1 | 4/2001 | LaFontaine et al. | 6,491,689 B1 | 12/2002 | Ellis et al. |
| 6,214,041 B1 | 4/2001 | Tweden et al. | 6,491,707 B2 | 12/2002 | Makower et al. |
| 6,217,527 B1 | 4/2001 | Selmon et al. | 6,506,408 B1 | 1/2003 | Palasis |
| 6,217,549 B1 | 4/2001 | Selmon et al. | 6,508,783 B2 | 1/2003 | DeVore |
| 6,217,575 B1 | 4/2001 | DeVore et al. | 6,508,824 B1 | 1/2003 | Flaherty et al. |
| 6,221,049 B1 | 4/2001 | Selmon et al. | 6,508,825 B1 | 1/2003 | Selmon et al. |
| 6,223,752 B1 | 5/2001 | Vanney et al. | 6,511,458 B2 | 1/2003 | Milo et al. |
| 6,224,584 B1 | 5/2001 | March et al. | 6,514,217 B1 | 2/2003 | Selmon et al. |
| 6,231,546 B1 | 5/2001 | Milo et al. | 6,514,271 B2 | 2/2003 | Evans et al. |
| 6,231,587 B1 | 5/2001 | Makower | 6,517,558 B2 | 2/2003 | Gittings et al. |
| 6,235,000 B1 | 5/2001 | Milo et al. | 6,524,323 B1 | 2/2003 | Nash et al. |
| 6,237,607 B1 | 5/2001 | Vanney et al. | 6,524,324 B1 | 2/2003 | Mueller et al. |
| 6,238,406 B1 | 5/2001 | Ellis et al. | 6,528,444 B1 | 3/2003 | Kondoh et al. |
| 6,241,667 B1 | 6/2001 | Vetter et al. | 6,533,779 B2 | 3/2003 | Kinsella et al. |
| 6,248,112 B1 | 6/2001 | Gambale et al. | 6,544,220 B2 | 4/2003 | Shuman et al. |
| 6,250,305 B1 | 6/2001 | Tweden | 6,544,230 B1 | 4/2003 | Flaherty et al. |
| 6,251,079 B1 | 6/2001 | Gambale et al. | 6,559,132 B1 | 5/2003 | Holmer |
| 6,251,116 B1 | 6/2001 | Shennib et al. | 6,561,998 B1 | 5/2003 | Roth et al. |
| 6,251,418 B1 | 6/2001 | Ahern et al. | 6,565,528 B1 | 5/2003 | Mueller |
| 6,253,768 B1 | 7/2001 | Wilk | 6,565,594 B1 | 5/2003 | Herweck et al. |
| 6,253,769 B1 | 7/2001 | LaFontaine et al. | 6,569,145 B1 | 5/2003 | Shmulewitz et al. |
| 6,254,564 B1 | 7/2001 | Wilk et al. | 6,569,147 B1 | 5/2003 | Evans et al. |
| 6,258,052 B1 | 7/2001 | Milo | 6,573,311 B1 | 6/2003 | Martakos et al. |
| 6,258,119 B1 | 7/2001 | Hussein et al. | 6,582,463 B1 | 6/2003 | Mowry et al. |
| 6,261,304 B1 | 7/2001 | Hall et al. | 6,587,718 B2 | 7/2003 | Talpade |
| 6,283,951 B1 | 9/2001 | Flaherty et al. | 6,605,053 B1 | 8/2003 | Kamm et al. |
| 6,283,983 B1 | 9/2001 | Makower et al. | 6,610,100 B2 | 8/2003 | Phelps et al. |
| 6,285,903 B1 | 9/2001 | Rosenthal et al. | 6,613,026 B1 | 9/2003 | Palasis et al. |
| 6,287,317 B1 | 9/2001 | Makower et al. | 6,616,626 B2 | 9/2003 | Crank et al. |
| 6,290,709 B1 | 9/2001 | Ellis et al. | 6,632,470 B2 | 10/2003 | Morra et al. |
| 6,290,719 B1 | 9/2001 | Garberoglio | 6,641,610 B2 | 11/2003 | Briefs et al. |
| 6,290,728 B1 | 9/2001 | Phelps et al. | 6,651,670 B2 | 11/2003 | Rapacki et al. |
| 6,302,875 B1 | 10/2001 | Makower et al. | 6,669,691 B1 | 12/2003 | Taimisto |
| 6,302,892 B1 | 10/2001 | Wilk | 6,669,709 B1 | 12/2003 | Cohn et al. |
| 6,322,548 B1 | 11/2001 | Payne et al. | 6,685,648 B2 | 2/2004 | Flaherty et al. |
| 6,330,884 B1 | 12/2001 | Kim | 6,685,716 B1 | 2/2004 | Flaherty et al. |
| 6,331,178 B1 | 12/2001 | Loeb et al. | 2001/0000041 A1 | 3/2001 | Selmon et al. |
| 6,344,027 B1 | 2/2002 | Goll | 2001/0004683 A1 | 6/2001 | Gambale et al. |
| 6,350,248 B1 | 2/2002 | Knudson et al. | 2001/0004690 A1 | 6/2001 | Gambale et al. |
| 6,352,543 B1 | 3/2002 | Cole | 2001/0004699 A1 | 6/2001 | Gittings et al. |
| 6,361,519 B1 | 3/2002 | Knudson et al. | 2001/0008969 A1 | 7/2001 | Evans et al. |
| 6,363,938 B2 | 4/2002 | Saadat et al. | 2001/0012924 A1 | 8/2001 | Milo et al. |
| 6,363,939 B1 | 4/2002 | Wilk | 2001/0012948 A1 | 8/2001 | Vanney |
| 6,375,615 B1 | 4/2002 | Flaherty et al. | 2001/0014813 A1 | 8/2001 | Saadat et al. |
| 6,379,319 B1 | 4/2002 | Garibotto et al. | 2001/0016700 A1 | 8/2001 | Eno et al. |
| 6,387,119 B2 | 5/2002 | Wolf et al. | 2001/0018596 A1 | 8/2001 | Selmon et al. |
| 6,390,098 B1 | 5/2002 | LaFontaine et al. | 2001/0020172 A1 | 9/2001 | Selmon et al. |
| 6,395,208 B1 | 5/2002 | Herweck et al. | 2001/0025643 A1 | 10/2001 | Foley |
| 6,402,740 B1 | 6/2002 | Ellis et al. | 2001/0027287 A1 | 10/2001 | Shmulewitz et al. |
| 6,406,488 B1 | 6/2002 | Tweden et al. | 2001/0029385 A1 | 10/2001 | Shennib et al. |
| 6,406,491 B1 | 6/2002 | Vanney | 2001/0034547 A1 | 10/2001 | Hall et al. |
| 6,409,697 B2 | 6/2002 | Eno et al. | 2001/0037117 A1 | 11/2001 | Gambale et al. |
| 6,409,751 B1 | 6/2002 | Hall et al. | 2001/0037149 A1 | 11/2001 | Wilk |
| 6,416,490 B1 | 7/2002 | Ellis et al. | 2001/0039426 A1 | 11/2001 | Makower et al. |
| 6,423,089 B1 | 7/2002 | Gingras et al. | 2001/0039445 A1 | 11/2001 | Hall et al. |
| 6,432,119 B1 | 8/2002 | Saadat | 2001/0041902 A1 | 11/2001 | Lepulu et al. |
| 6,432,126 B1 | 8/2002 | Gambale et al. | 2001/0044631 A1 | 11/2001 | Akin et al. |
| 6,432,127 B1 | 8/2002 | Kim et al. | 2001/0047165 A1 | 11/2001 | Makower et al. |
| 6,432,132 B1 | 8/2002 | Cottone et al. | 2001/0047197 A1 | 11/2001 | Foley |
| 6,443,158 B1 | 9/2002 | LaFontaine et al. | 2001/0049523 A1 | 12/2001 | DeVore et al. |
| 6,447,522 B2 | 9/2002 | Gambale et al. | 2001/0053932 A1 | 12/2001 | Phelps et al. |
| 6,447,539 B1 | 9/2002 | Nelson et al. | | | |

| | | |
|---|---|---|
| 2002/0002349 A1 | 1/2002 | Flaherty et al. |
| 2002/0004662 A1 | 1/2002 | Wilk |
| 2002/0004663 A1 | 1/2002 | Gittings et al. |
| 2002/0007138 A1 | 1/2002 | Wilk et al. |
| 2002/0029079 A1 | 3/2002 | Kim et al. |
| 2002/0032476 A1 | 3/2002 | Gambale et al. |
| 2002/0032478 A1 | 3/2002 | Boekstegers et al. |
| 2002/0033180 A1 | 3/2002 | Solem |
| 2002/0049486 A1 | 4/2002 | Knudson et al. |
| 2002/0049495 A1 | 4/2002 | Kutryk et al. |
| 2002/0058897 A1 | 5/2002 | Renati |
| 2002/0062146 A1 | 5/2002 | Makower et al. |
| 2002/0065478 A1 | 5/2002 | Knudson et al. |
| 2002/0072699 A1 | 6/2002 | Knudson et al. |
| 2002/0072758 A1 | 6/2002 | Reo et al. |
| 2002/0077566 A1 * | 6/2002 | Laroya et al. ............... 600/585 |
| 2002/0077654 A1 | 6/2002 | Javier, Jr. et al. |
| 2002/0082546 A1 | 6/2002 | Crank et al. |
| 2002/0092535 A1 | 7/2002 | Wilk |
| 2002/0092536 A1 | 7/2002 | LaFontaine et al. |
| 2002/0095110 A1 | 7/2002 | Vanney et al. |
| 2002/0095111 A1 | 7/2002 | Tweden et al. |
| 2002/0099392 A1 | 7/2002 | Mowry et al. |
| 2002/0099404 A1 | 7/2002 | Mowry |
| 2002/0100484 A1 | 8/2002 | Wolf et al. |
| 2002/0103459 A1 | 8/2002 | Sparks et al. |
| 2002/0103495 A1 | 8/2002 | Cole |
| 2002/0103534 A1 | 8/2002 | Vanney et al. |
| 2002/0111644 A1 | 8/2002 | Shuman et al. |
| 2002/0111672 A1 | 8/2002 | Kim et al. |
| 2002/0123698 A1 | 9/2002 | Garibotto et al. |
| 2002/0123786 A1 | 9/2002 | Gittings et al. |
| 2002/0138087 A1 | 9/2002 | Shennib et al. |
| 2002/0143285 A1 | 10/2002 | Eno et al. |
| 2002/0143289 A1 | 10/2002 | Ellis et al. |
| 2002/0143347 A1 | 10/2002 | Cole et al. |
| 2002/0144696 A1 | 10/2002 | Sharkawy et al. |
| 2002/0161383 A1 | 10/2002 | Akin et al. |
| 2002/0161424 A1 * | 10/2002 | Rapacki et al. ............... 623/1.1 |
| 2002/0165479 A1 | 11/2002 | Wilk |
| 2002/0165606 A1 | 11/2002 | Wolf et al. |
| 2002/0179098 A1 | 12/2002 | Makower et al. |
| 2002/0183716 A1 | 12/2002 | Herweck et al. |
| 2002/0193782 A1 | 12/2002 | Ellis et al. |
| 2003/0015816 A1 | 1/2003 | Rapacki et al. |
| 2003/0018379 A1 | 1/2003 | Knudson et al. |
| 2003/0044315 A1 | 3/2003 | Boekstegers |
| 2003/0045828 A1 | 3/2003 | Wilk |
| 2003/0055371 A1 | 3/2003 | Wolf et al. |
| 2003/0062650 A1 | 4/2003 | Martakos et al. |
| 2003/0073973 A1 | 4/2003 | Evans et al. |
| 2003/0078561 A1 | 4/2003 | Gambale et al. |
| 2003/0078562 A1 | 4/2003 | Makower et al. |
| 2003/0100920 A1 | 5/2003 | Akin et al. |
| 2003/0105514 A1 | 6/2003 | Phelps et al. |
| 2003/0120195 A1 | 6/2003 | Milo et al. |
| 2003/0120259 A1 | 6/2003 | Mickley |
| 2003/0125798 A1 | 7/2003 | Martin |
| 2003/0163198 A1 | 8/2003 | Morra et al. |
| 2003/0181938 A1 | 9/2003 | Roth et al. |
| 2003/0195458 A1 | 10/2003 | Phelps et al. |
| 2003/0204160 A1 | 10/2003 | Kamm et al. |
| 2003/0212413 A1 | 11/2003 | Wilk |
| 2003/0216679 A1 | 11/2003 | Wolf et al. |
| 2003/0236542 A1 | 12/2003 | Makower |
| 2004/0006298 A1 | 1/2004 | Wilk |
| 2004/0006301 A1 | 1/2004 | Sell et al. |
| 2004/0015225 A1 | 1/2004 | Kim et al. |

FOREIGN PATENT DOCUMENTS

| | | |
|---|---|---|
| EP | 0 797 958 A1 | 10/1997 |
| EP | 0 799 604 A1 | 10/1997 |
| EP | 0 801 928 A1 | 10/1997 |
| EP | 0 824 903 | 2/1998 |
| EP | 0 829 239 A1 | 3/1998 |
| EP | 0 836 834 A2 | 4/1998 |
| EP | 0 853 921 A2 | 7/1998 |
| EP | 0 858 779 A1 | 8/1998 |
| EP | 0 876 796 A2 | 11/1998 |
| EP | 0 876 803 | 11/1998 |
| EP | 0 815 798 A2 | 1/1999 |
| EP | 0 888 750 A1 | 1/1999 |
| EP | 0 895 752 A1 | 2/1999 |
| EP | 0 903 123 | 3/1999 |
| EP | 0 904 745 | 3/1999 |
| EP | 0 934 728 A2 | 8/1999 |
| EP | 0 955 017 | 11/1999 |
| EP | 0 955 019 | 11/1999 |
| EP | 0 962 194 | 12/1999 |
| EP | 1 020 166 | 7/2000 |
| EP | 1 027 870 | 8/2000 |
| EP | 1 027 878 | 8/2000 |
| EP | 1 088 564 A1 | 4/2001 |
| EP | 1 097 676 | 5/2001 |
| EP | 1 166 721 | 1/2002 |
| EP | 0 959 815 B1 | 12/2002 |
| EP | 1 112 097 B1 | 6/2003 |
| GB | 2316322 | 10/1998 |
| WO | WO 94/16629 | 8/1994 |
| WO | 94/169629 | 8/1994 |
| WO | WO 96/35469 | 11/1996 |
| WO | WO 96/39962 | 12/1996 |
| WO | WO 96/39964 | 12/1996 |
| WO | WO 96/39965 | 12/1996 |
| WO | 97/13463 | 4/1997 |
| WO | 97/13471 | 4/1997 |
| WO | WO 97/18768 | 5/1997 |
| WO | 97/27893 | 8/1997 |
| WO | 97/27897 | 8/1997 |
| WO | 97/27898 | 8/1997 |
| WO | WO 97/27898 | 8/1997 |
| WO | 97/32551 | 9/1997 |
| WO | WO 97/41916 | 11/1997 |
| WO | 97/41916 | 11/1997 |
| WO | WO 97/43961 | 11/1997 |
| WO | WO 98/02099 | 1/1998 |
| WO | WO 98/03118 | 1/1998 |
| WO | 98/06356 | 2/1998 |
| WO | 98/08456 | 3/1998 |
| WO | 98/10714 | 3/1998 |
| WO | 98/16161 | 4/1998 |
| WO | WO 98/17185 | 4/1998 |
| WO | WO 98/19607 | 5/1998 |
| WO | WO 98/24373 | 6/1998 |
| WO | WO 98/25533 | 6/1998 |
| WO | WO 98/38916 | 9/1998 |
| WO | WO 98/38925 | 9/1998 |
| WO | WO 98/38939 | 9/1998 |
| WO | WO 98/38941 | 9/1998 |
| WO | WO 98/39038 | 9/1998 |
| WO | WO 98/44869 | 10/1998 |
| WO | 98/46115 | 10/1998 |
| WO | 98/46119 | 10/1998 |
| WO | WO 98/49964 | 11/1998 |
| WO | WO 98/53759 | 12/1998 |
| WO | WO 98/55027 | 12/1998 |
| WO | WO 98/57590 | 12/1998 |
| WO | WO 98/57591 | 12/1998 |

| | | |
|---|---|---|
| WO | WO 98/57592 | 12/1998 |
| WO | 98/08624 | 2/1999 |
| WO | WO 99/07296 | 2/1999 |
| WO | WO 99/15220 | 4/1999 |
| WO | WO 99/17671 | 4/1999 |
| WO | 99/17683 | 4/1999 |
| WO | 99/21490 | 5/1999 |
| WO | WO 99/21510 | 5/1999 |
| WO | WO 99/22655 | 5/1999 |
| WO | WO 99/22658 | 5/1999 |
| WO | 99/25273 | 5/1999 |
| WO | WO 99/27985 | 6/1999 |
| WO | WO 99/32051 | 7/1999 |
| WO | WO 99/35977 | 7/1999 |
| WO | WO 99/35979 | 7/1999 |
| WO | WO 99/35980 | 7/1999 |
| WO | 99/36000 | 7/1999 |
| WO | 99/36001 | 7/1999 |
| WO | WO 99/37218 | 7/1999 |
| WO | 99/38459 | 8/1999 |
| WO | WO 99/40853 | 8/1999 |
| WO | 99/40868 | 8/1999 |
| WO | WO 99/40963 | 8/1999 |
| WO | WO 99/44524 | 9/1999 |
| WO | WO 99/47071 | 9/1999 |
| WO | WO 99/47078 | 9/1999 |
| WO | WO 99/48427 | 9/1999 |
| WO | 99/48545 | 9/1999 |
| WO | WO 99/48549 | 9/1999 |
| WO | 99/49790 | 10/1999 |
| WO | 99/49793 | 10/1999 |
| WO | 99/49910 | 10/1999 |
| WO | 99/51162 | 10/1999 |
| WO | 99/52481 | 10/1999 |
| WO | 99/53863 | 10/1999 |
| WO | 99/55406 | 11/1999 |
| WO | 96/62430 | 12/1999 |
| WO | 99/60941 | 12/1999 |
| WO | 00/09195 | 2/2000 |
| WO | WO 00/10623 | 3/2000 |
| WO | 00/12029 | 3/2000 |
| WO | WO 00/13722 | 3/2000 |
| WO | 00/15146 | 3/2000 |
| WO | 00/15147 | 3/2000 |
| WO | 00/15148 | 3/2000 |
| WO | 00/15149 | 3/2000 |
| WO | 00/15275 | 3/2000 |
| WO | 00/18302 | 4/2000 |
| WO | WO 00/18323 | 4/2000 |
| WO | WO 00/18325 | 4/2000 |
| WO | WO 00/18326 | 4/2000 |
| WO | WO 00/18331 | 4/2000 |
| WO | WO 00/18462 | 4/2000 |
| WO | 00/21436 | 4/2000 |
| WO | 00/21461 | 4/2000 |
| WO | 00/21463 | 4/2000 |
| WO | 00/24449 | 5/2000 |
| WO | 00/33725 | 6/2000 |
| WO | WO 00/35376 | 6/2000 |
| WO | WO 00/36997 | 6/2000 |
| WO | 00/41632 | 7/2000 |
| WO | 00/41633 | 7/2000 |
| WO | WO 00/43051 | 7/2000 |
| WO | 00/45711 | 8/2000 |
| WO | WO 00/45886 | 8/2000 |
| WO | WO 00/49952 | 8/2000 |
| WO | WO 00/49954 | 8/2000 |
| WO | WO 00/49956 | 8/2000 |
| WO | WO 00/54660 | 9/2000 |
| WO | WO 00/54661 | 9/2000 |
| WO | WO 00/56224 | 9/2000 |
| WO | WO 00/56225 | 9/2000 |
| WO | 00/56387 | 9/2000 |
| WO | 00/66007 | 11/2000 |
| WO | 00/66009 | 11/2000 |
| WO | 00/66035 | 11/2000 |
| WO | WO 00/69345 | 11/2000 |
| WO | WO 00/69504 | 11/2000 |
| WO | 00/71195 | 11/2000 |
| WO | WO 01/08566 A1 | 2/2001 |
| WO | WO 01/08602 | 2/2001 |
| WO | WO 01/08602 A1 | 2/2001 |
| WO | 01/10340 | 2/2001 |
| WO | 01/10341 | 2/2001 |
| WO | 01/10347 | 2/2001 |
| WO | 01/10348 | 2/2001 |
| WO | 01/10349 | 2/2001 |
| WO | WO 01/10350 A1 | 2/2001 |
| WO | 01/17440 | 3/2001 |
| WO | 01/17456 | 3/2001 |
| WO | WO 01/23016 A1 | 4/2001 |
| WO | WO 01/26562 | 4/2001 |
| WO | WO 01/41657 A1 | 6/2001 |
| WO | 01/49187 | 7/2001 |
| WO | WO 01/54625 | 8/2001 |
| WO | 01/60427 | 8/2001 |
| WO | WO 01/68158 A1 | 9/2001 |
| WO | WO 01/70133 | 9/2001 |
| WO | WO 01/72239 A2 | 10/2001 |
| WO | 01/78801 | 10/2001 |
| WO | 01/82803 | 11/2001 |
| WO | 01/82837 | 11/2001 |
| WO | WO 02/02163 | 1/2002 |
| WO | 02/11647 | 2/2002 |
| WO | WO 02/11807 A2 | 2/2002 |
| WO | WO 02/13698 A1 | 2/2002 |
| WO | WO 02/13699 A1 | 2/2002 |
| WO | WO 02/13703 A1 | 2/2002 |
| WO | WO 02/13704 A1 | 2/2002 |
| WO | WO 02/24108 A2 | 3/2002 |
| WO | WO 02/24247 A1 | 3/2002 |
| WO | WO 02/24248 A1 | 3/2002 |
| WO | WO 02/26310 A1 | 4/2002 |
| WO | WO 02/26462 A1 | 4/2002 |
| WO | WO 02/30325 A2 | 4/2002 |
| WO | WO 02/30326 A2 | 4/2002 |
| WO | WO 02/30330 A2 | 4/2002 |
| WO | WO 02/32330 A2 | 4/2002 |
| WO | WO 02/34323 A2 | 5/2002 |
| WO | WO 02/45598 A2 | 6/2002 |
| WO | WO 02/49695 A2 | 6/2002 |
| WO | WO 02/056937 A2 | 7/2002 |
| WO | WO 02/058567 A2 | 8/2002 |
| WO | WO 02/058591 A2 | 8/2002 |
| WO | WO 02/060509 | 8/2002 |
| WO | WO 02/062265 A2 | 8/2002 |
| WO | WO 02/064020 A2 | 8/2002 |
| WO | WO 02/091958 A2 | 11/2002 |
| WO | WO 03/028522 A2 | 4/2003 |
| WO | WO 2004/000170 A1 | 12/2003 |

OTHER PUBLICATIONS

Palmaz et al., "Expandable Intrahepatic Portacaval Shunt Stents in Dogs with Chronic Portal Hypertension," *AJR*, 1986, vol. 147, pp. 1251–1254.

Richter, M.D. et al., "Tranjugular Intrahepatic Portacaval Stent Shunt: Preliminary Clincal Results," *Radiology*, 1990, vol. 174, No. 3, pp. 1027–1030.-

Zemel, M.D. et al., "Percutaneous Transjugular Portosystemic Shunt," *JAMA*, 1991, vol. 266, No. 3, pp. 390–393

Massimo, M.D. et al., "Myocardial Revascularization by a New Method of Carrying Blood Directly from the Left Ventricular Cavity into the Coronary Circulation," *Journal of Thoracic Sueons*, Aug. 1997, vol. 34, No. 2, pp. 257–264.

Lary, M.D. et al., "Myocardial Revascularization Experiments Using the Epicardium," *Archives of Surgery*, Jan. 1969, vol. 98, No. 1, pp. 69–72.

Munro, M.D. et al., "The Possibility of myocardial revascularization by creation of a left ventriculocoronary artery fistula," *Journal of Thoracic and Cardiovascular Surgery*, Jul. 1969, vol. 58, No. 1, pp. 25–32.

Kuzela, M.D. et al., "Experimental evaluation to direct transventricular revascularization," *The Journal of Thoracic and Cardiovascular Surgery*, Jun. 1969, vol. 57, No. 6, pp. 770–773.

* cited by examiner

METHODS AND DEVICES FOR DELIVERING A VENTRICULAR STENT

CROSS REFERENCE TO RELATED APPLICATIONS

This application claims the benefits of U.S. Provisional Patent Application Ser. No. 60/201,732, filed May 4, 2000.

BACKGROUND OF THE INVENTION

1. Field of the Invention

The present invention relates to methods and related devices for forming a passageway in a heart wall and delivering a stent therein to supply oxygenated blood flow to vascular structure from a chamber of the heart. For example, the methods and related devices preferably place a stent in the left ventricular heart wall in order to establish a supply of blood from the left ventricle to the coronary artery at a point distal a partial or total occlusion of the artery.

2. Background of the Related Art

A prevalent form of heart failure involves the build-up of plaque on walls of various vascular structure, such as, for example, the coronary artery. The plaque that builds up on the walls can form either a partial or total occlusion in the artery. Such an occlusion may either limit or completely block blood flow through the artery, which typically enters through the aortic valve from the left ventricle. Because the coronary artery supplies blood to the various blood vessels within the muscle forming the heart wall, limiting or blocking of the blood flow through the coronary artery can result in damage to the heart muscle, such as, for example, necrosis. Necrotic tissue can lead to reduced cardiac function by diminishing the pumping capacity of the heart. In some instances, the diminished capacity of the heart can lead to heart attack.

Various techniques have been developed to treat this type of heart condition. For example, a surgical technique, referred to as coronary artery bypass grafting (CABG), involves removing a vein or portion thereof from the patient, usually from the femoral vein, and grafting the vein so as to connect portions of the coronary artery upstream and downstream of the occlusion. Thus, the blood flow is directed around the occlusion and through the vein graft so that the oxygenated blood can be delivered to the vessels in the heart wall. CABG generally is performed as an open surgery resulting in relatively long recovery times. Patients also often experience a large amount of discomfort resulting from harvesting of the veins to be used in CABG. Furthermore, the veins that are grafted to the coronary artery have a limited useful life.

Coronary angioplasty represents another form of treatment of arteries having occlusions that can be performed as an alternative to bypass surgery. In this technique, a balloon catheter is inserted percutaneously into the coronary artery. Once the catheter has been inserted such that the balloon is adjacent the occlusion being treated, the balloon is inflated to dilate the artery in the location of the occlusion. Often this technique involves inflating and deflating the balloon repeatedly to establish the desired dilation of the artery. This technique may include placing a stent in a collinear manner in the artery at the location of the occlusion to maintain the proper dilation of the artery. Delivery of the stent can be accomplished by removing the dilation balloon catheter and then inserting a balloon carrying the stent. A multiple balloon stent delivery catheter may dilate the artery and place the stent in a single insertion of the catheter into the patient.

Another technique that has been used to bypass a partial or total occlusion of the artery includes implanting a stent, or otherwise creating a flow passage, in the myocardial wall between the left ventricle and coronary artery at a position downstream of the occlusion. In this technique, a portion of the blood pumped from the left ventricle flows directly into the coronary artery.

SUMMARY OF THE INVENTION

The advantages and purpose of the invention will be set forth in part in the description which follows, and in part will be obvious from the description, or may be learned by practice of the invention. The advantages and purpose of the invention will be realized and attained by means of the elements and combinations particularly pointed out in the appended claims.

The present invention pertains to methods, and related tools for performing the method, of delivering a stent or other like-device to the heart to connect the left ventricle to the coronary artery to thereby supply blood directly from the ventricle to the coronary artery. In a preferred embodiment, a method may be used to bypass a total or partial occlusion of a coronary artery. The inventive method is relatively quicker and less invasive than other techniques as a result, for example, of the manner in which the device is implanted into the heart and the elimination of the need to harvest veins from the patient to perform a CABG. Moreover, the delivery technique according to an embodiment of the present invention facilitates connecting the ventricle and coronary artery via a stent, the technique ultimately reducing the risk of damage to the coronary artery, as will be explained.

An aspect of the invention includes a method to provide direct blood flow between a heart chamber and a coronary vessel. The method includes placing a guide device through an anterior wall and a posterior wall of the coronary vessel and through a heart wall between the heart chamber and the coronary vessel, forming a passageway in the heart wall at a location defined by the guide device, and placing a stent within the passageway. The method may include insertion of a hollow needle through the anterior wall and the posterior wall of the coronary vessel and through the heart wall, prior to placing the guide device. The guide device may be, for example, a guidewire or other suitable like guide mechanism. According to an aspect of the invention, placing the guide device includes inserting the guidewire through the hollow needle until an end of the guidewire rests in the heart chamber. The hollow needle may be removed after inserting the guidewire through the hollow needle.

According to another aspect of the invention, the method may also include measuring a depth of insertion of the hollow needle. The measuring may be accomplished by viewing markings on the hollow needle that indicate the depth of insertion of the hollow needle or determining a pressure differential between the heart chamber and exterior the heart chamber.

The method according to another aspect of the present invention also includes avoiding intracardiac structures during insertion of the hollow needle, and placing the guide device at a predetermined angle relative to the posterior wall of the coronary vessel, which may include inserting a hollow needle at the predetermined angle through the anterior wall and the posterior wall of the coronary vessel and the heart wall, prior to placing the guide device.

In an aspect of a method of the present invention, the passageway is formed with a dilation device, such as a sheath or an inflation device, which may be in the form of a balloon for example. Forming the passageway may include inserting a balloon into the location defined by the guide device and inflating the balloon. A catheter may carry the balloon over the guide device. The balloon is preferably deflated after forming the passageway and removed from the passageway after deflation.

In another aspect of the invention, a stent is placed with an inflation device. The inflation device may be a balloon that carries the stent, and placing the stent includes inserting the balloon and the stent within the passageway and inflating the balloon. A catheter may carry the balloon and the stent over the guide device.

In another embodiment of the present invention, the passageway is formed and the stent is placed by a catheter carrying a first inflation device and a second inflation device. The first inflation device may be a first balloon and the second inflation device may be a second balloon. The catheter is inserted over the guide device so that the first balloon is positioned in the location defined by the guide device. The first balloon is inflated to form the passageway and deflated after forming the passageway. The catheter then is further inserted over the guide device so that the second balloon is positioned in the passageway. The second balloon may carry a stent. The second balloon is inflated to place the stent within the passageway.

According to another aspect, the invention includes a method of providing direct blood flow between a heart chamber and a coronary vessel that includes inserting an inflation device through an anterior wall and a posterior wall of the coronary vessel and into the heart wall, inflating the inflation device within the heart wall to form a passageway between the heart chamber and the coronary vessel, and placing a stent within the passageway. Inserting the inflation device may include inserting the inflation device over a guide device extending between the heart wall and exterior the heart chamber and the coronary vessel.

Yet another aspect of the invention includes a device for measuring the depth of penetration from an anterior wall of a coronary vessel to a heart chamber. The device includes a hollow needle defining a lumen and having a distal end and a proximal end. A depth indication mechanism is disposed on an external surface of the hollow needle and a handle is disposed on the proximal end of the needle. The handle includes an inner portion in flow communication with the hollow needle and a portion of the handle is transparent so that blood from the left ventricle that enters the handle from the lumen of the needle can be observed.

According to yet another aspect of the invention, a device for placing a stent in a heart wall comprises a delivery tool configured to deliver the stent to a location within the heart wall and a stop mechanism disposed on the delivery tool such that the stop mechanism is proximate at least one end of the stent during delivery of the stent. The stop mechanism may be configured to engage a surface to determine the placement location of the stent within the heart wall.

According to another aspect, the invention includes a device for placement in a passageway between a heart chamber and a coronary vessel. The device includes a hollow conduit and a plurality of extensions protruding from an end of the conduit. The plurality of extensions can include a pair of extensions at opposite sides of the conduit.

The foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate embodiments of the invention and together with the description, serve to explain the principles of the invention.

DESCRIPTION OF THE PREFERRED EMBODIMENTS

An aspect of the present invention includes a novel method of placing a stent within the heart wall between the left ventricle and the coronary artery to provide blood flow directly therebetween. The novel method generally includes the steps of establishing a position of a passageway between the left ventricle and the coronary artery, creating the passageway, and placing a stent in the passageway. Each of these general steps will be described in greater detail below.

Although the methods according to the invention will be described with reference to establishing direct blood flow between the left ventricle and left anterior descending coronary artery, connections between other heart structures and vessels to establish flow therebetween also are within the scope of the invention. In addition, the inventive methods may be used in other settings, aside from the heart, that require creating a passage or conduit and delivering a device into the created passage to establish direct flow communication between two volumes, especially between volumes that may be difficult to access.

Figure 1:
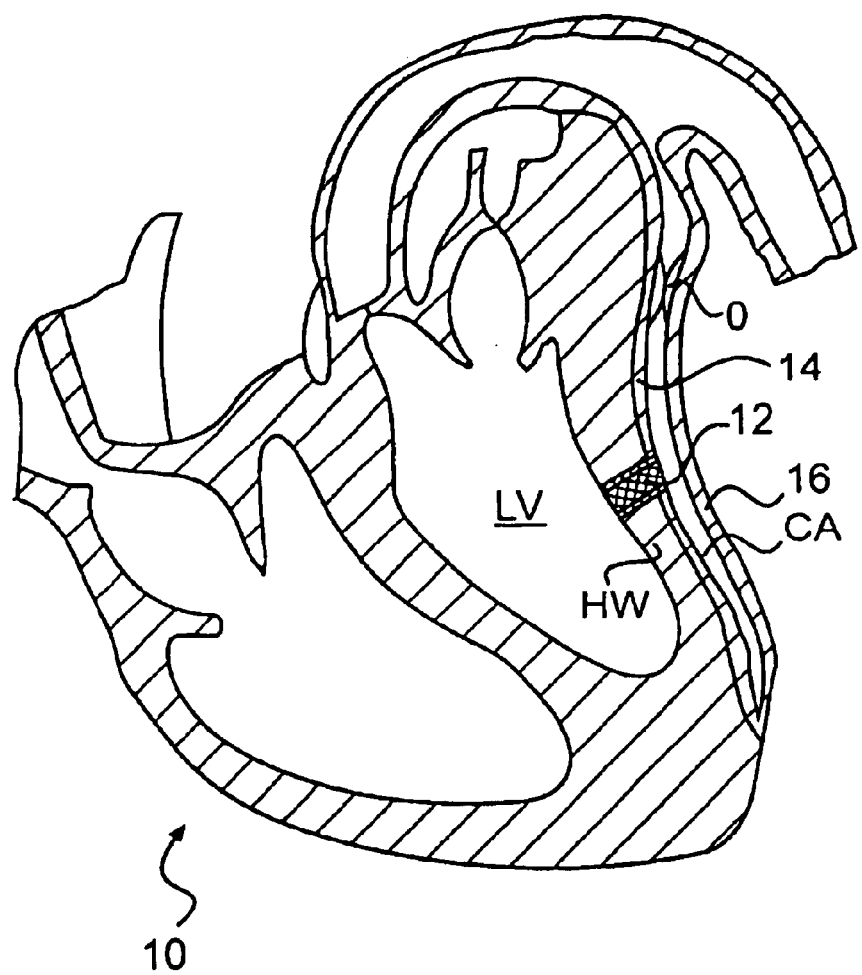
FIG. 1 is a cross-sectional view of a heart with a stent disposed in the heart wall between the left ventricle and coronary artery downstream of an occlusion in the coronary artery.

FIG. 1 generally shows a cross-sectional view of a heart 10 implanted with a conduit 12, preferably in the form of a stent. As shown, conduit 12 extends between the left ventricular chamber LV and the coronary artery CA at a point downstream of an occlusion O of coronary artery CA. Conduit 12 preferably does not extend substantially into either the left ventricle LV or the coronary artery CA. The invention includes other possible connection positions between the left ventricle LV and coronary artery CA, such as, for example, an angled position of conduit 12 with respect to either the left ventricle LV or the coronary artery CA. It is important that the connection position is selected so as to avoid interference with various structures in the heart, including the papillary muscles, chordae, and mitral valve.

Once implanted, conduit 12 extends from the posterior wall 14 of the coronary artery CA to the left ventricle LV. The posterior wall 14 refers to that portion of the arterial wall that interfaces with the heart wall. The anterior wall 16 of the coronary artery refers to a portion of the arterial wall that does not interface with the heart wall. In one preferred embodiment, conduit 12 lies substantially flush with the interface between posterior wall 14 of coronary artery CA and the exterior surface of heart wall HW surrounding left ventricle LV, as negative effects may result if conduit 12 protrudes into coronary artery CA or is recessed within the myocardium. For example, if conduit 12 protrudes too far into coronary artery CA, blood flow through coronary artery CA, as well as blood flow exiting conduit 12 may become disturbed, resulting in stasis. On the other hand, if conduit 12 is recessed within the myocardium such that a space remains between conduit 12 and posterior wall 14 of the CA, the space may become occluded with tissue, thereby preventing flow into CA.

Figure 4:
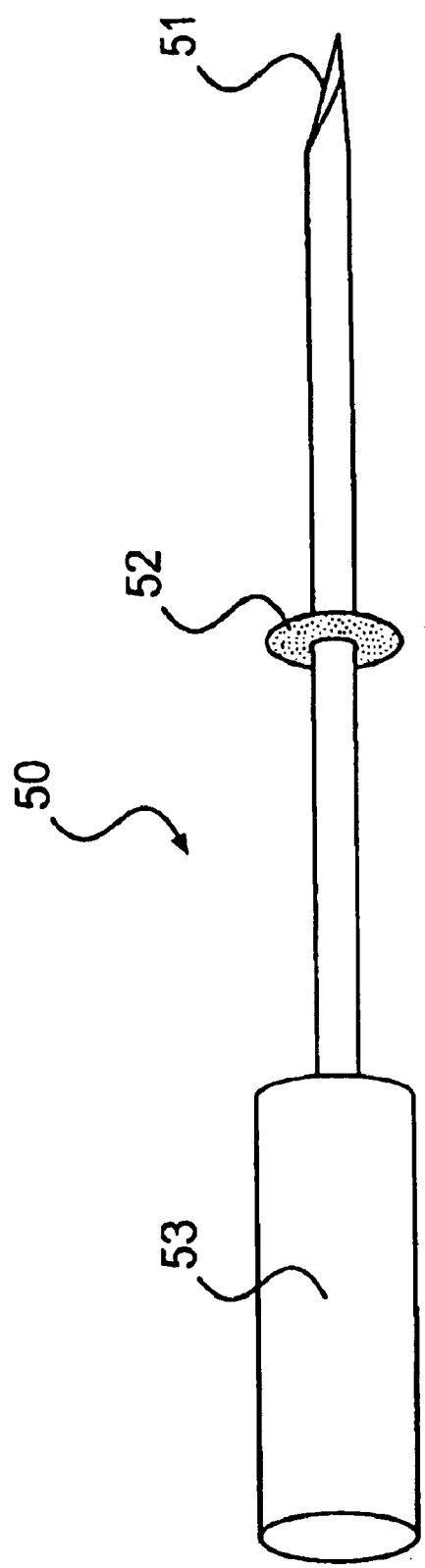
FIG. 4 is a device according to an embodiment of the present invention for use in accessing a heart chamber through a coronary vessel and for measuring the depth of penetration from the coronary vessel to the heart chamber.

The method according to an embodiment of the present invention includes forming a passage in the heart wall and implanting a conduit 12, preferably in the form of a collapsible stent, in the passage to establish direct flow communication between the left ventricular chamber and the left anterior descending coronary artery. In a preferred method of the present invention, a first step includes providing access to the location of the heart wall at which the stent 12 will be implanted. According to the invention, access to the heart wall surrounding the left ventricle LV is obtained from outside the coronary artery CA. A hollow needle 50, shown in FIG. 4, is used to puncture the anterior wall 16 of the coronary artery. Sharpened distal end 51 of needle 50 is advanced until it punctures the posterior wall 14 of the coronary artery at a position that coincides with the location at which the stent 12 will be implanted into the heart wall surrounding the left ventricle LV. Needle 50 is then inserted into and advanced through the heart wall HW until a reflux of blood into needle 50 occurs, indicating that needle 50 has entirely traversed the heart wall and entered the left ventricle LV. At least a portion of hollow needle 50 that remains external to coronary artery CA during insertion into the left ventricle LV, for instance a portion of handle 53, should be transparent to permit observation of the reflux of blood into the needle.

Insertion of the needle should avoid damaging or otherwise interfering with critical internal cardiac structures such as, for example, the papillary muscles, chordae, the mitral valve, etc. To avoid such damage, a visualization technique may be employed either prior to insertion of the needle or concurrently with the insertion of the needle. Such visualization techniques can include, for example, the use of transesophogeal, intraventricular, intracardiac, or epicardial ultrasonic probes, or a combination thereof.

Figure 2:
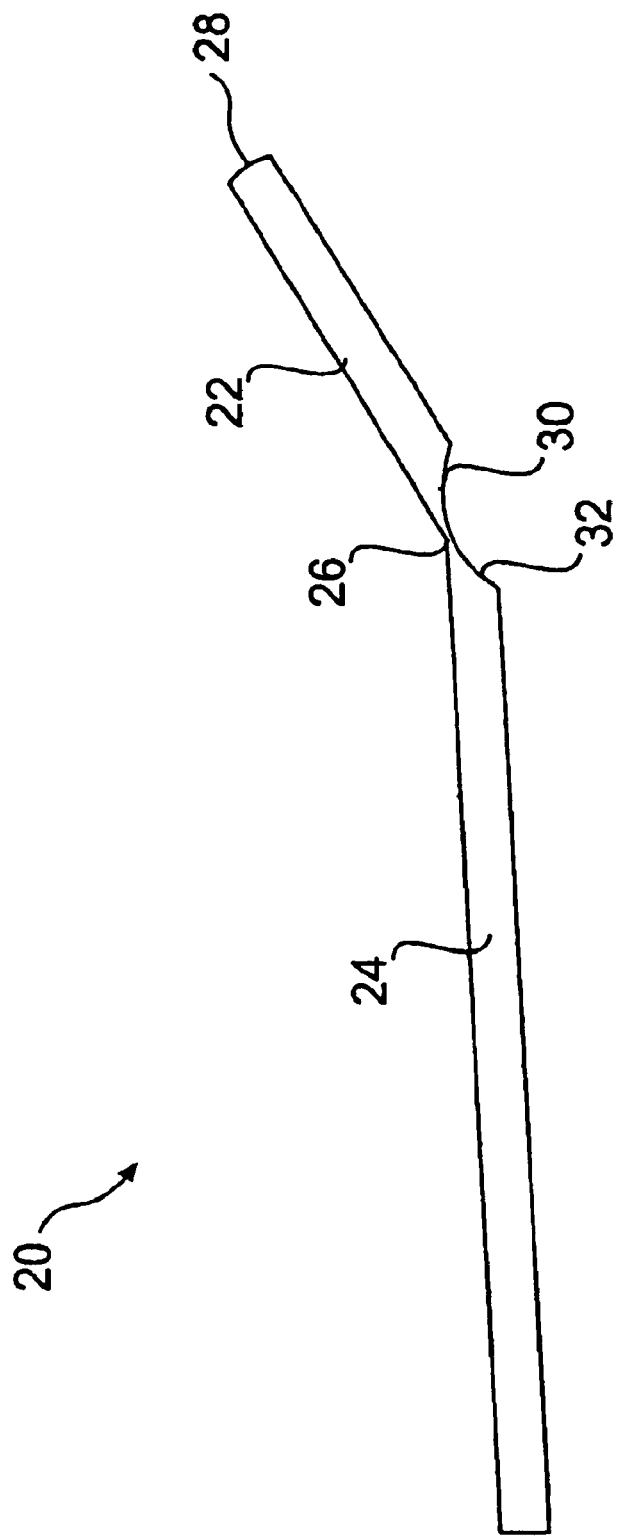
FIG. 2 is an embodiment of a positioning tool for use in a method according to an embodiment of the present invention.

In a preferred form of the invention, the stent 12 will be implanted at an angle in the heart wall. The angle of the stent 12 to the heart wall preferably is chosen according to fluid flow analyses that seek to optimize the blood flow path from the left ventricle to the coronary artery and minimize energy losses due to poor entry and exit angles, and the like. In the case of an angularly implanted stent, hollow needle 50 also will have to enter the heart wall at the appropriate angle. To properly angle hollow needle 50, a positioning tool preferably is employed. A preferred embodiment of such a positioning tool is shown in FIG. 2. Positioning tool 20 is a hollow tube preferably made of a substantially rigid material. Positioning tool 20 includes a first portion 22 connected to a second portion 24 at a hinge 26. First portion 22 has opposite ends 28, 30, and second portion 24 has an end 32 opposing end 30 and another end not shown in FIG. 2. In use, portion 22 is inserted into the coronary artery and portion 24 extends outside of the heart with end 32 open and facing towards the posterior wall of the coronary artery and the heart wall. The user bends portion 24 relative to portion 22 at hinge 26 so that portions 22 and 24 are at an appropriate angle. The user then can insert the hollow needle through portion 24 and into the heart wall at the desired angle.

After hollow needle 50 has punctured both the anterior and posterior walls of coronary artery CA, and has traversed the heart wall to enter into left ventricle LV, it may be desirable to measure the depth of penetration of the needle and thereby determine the thickness of the heart wall from the depth of needle penetration. This determination will be used later when, for example, choosing an appropriate balloon length for forming a passage between the left ventricle and the coronary artery, and choosing an appropriate length conduit to place in the passage. Therefore, on its external surface, the needle is provided with a depth indication mechanism. A preferable depth indication mechanism includes providing graduated markings representing various lengths on a proximal end of the needle. Once the needle penetrates through the ventricular wall and into the chamber, causing a reflux of blood through the needle, the depth of penetration is measured by the marking adjacent the anterior wall of the coronary artery. To then determine the thickness of the ventricular wall, the diameter of the coronary artery at the insertion site must be subtracted from the depth of needle penetration. This coronary artery diameter may be determined preoperatively by appropriate imaging techniques. Preferably, the preoperative image will show the location of the occlusion, the appropriate location for insertion of the needle, and the coronary artery diameter at that location.

An alternative depth indication mechanism includes an indicator 52 slidably disposed on needle 50. An example of such an indicator is shown in FIG. 4. Marker 52 defines an aperture through which needle 50 is inserted. The aperture preferably is sized such that marker 52 easily, yet controllably, slides along the length of the needle. That is, the aperture preferably is sized such that marker 52 frictionally engages with the needle and thus cannot slide along the needle unless a sufficient force is applied to the marker. Marker 52 abuts the anterior wall 16 of the coronary artery CA and slides along the length of the needle as the needle is inserted into the left ventricle LV. After needle 50 is removed, the depth of penetration is indicated by measuring the length from the distal end of needle 50 to marker 52. As a further alternative, graduated markings could be provided on the needle along with the marker to assist in determining the depth of penetration. Again, the actual thickness of the ventricular wall is determined by subtracting the diameter of the coronary artery (which preferably is determined using a visualization technique, such as echocardiography for example) from the depth of penetration measurement.

As a further alternative device and method for aiding the accurate determination of the depth of needle insertion, the needle may include a suitable pressure transducer at the tip of the needle. The pressure transducer would sense the pressure of the left ventricle to accurately indicate when the needle enters the left ventricle. Once such a pressure is indicated, the depth of penetration is determined by the graduated markings on the outside of the needle, as explained above.

Figure 5:
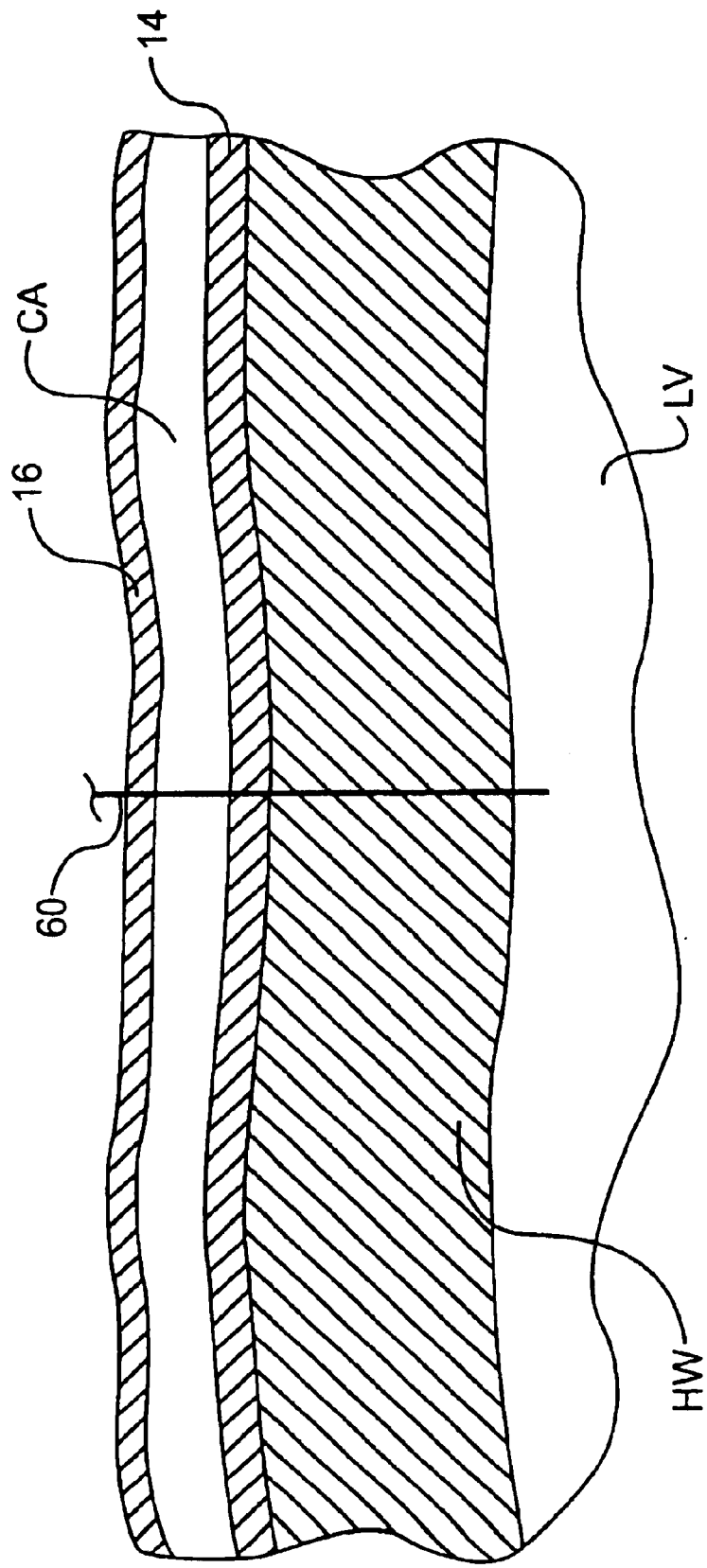
FIG. 5 is an embodiment of a guidewire placed, according to a method of the present invention, so as to provide access to the left ventricle through the coronary artery anterior and posterior walls.

After hollow needle 50 has been inserted through the coronary artery CA and heart wall, and into the left ventricle LV, such that a path having the desired angle and positioning relative to internal heart structures has been created, a guidewire 60 or other suitable guide device is placed within the lumen of hollow needle 50 and extended therethrough. The guidewire 60 preferably has a tip portion which is relatively flexible while the portion of the guidewire to be positioned in the myocardium preferably is relatively stiff. After the guidewire has been extended between the left ventricular chamber LV and external to the anterior wall of the coronary artery CA, the needle can be removed by sliding it off the guidewire. The placement of guidewire 60 allows a pathway to be maintained so that the myocardium and left ventricular chamber can be accessed from outside the heart. FIG. 5 shows a suitable placement of guidewire 60 with respect to the heart after the needle has been removed.

The next step of an embodiment of the inventive method includes forming a passageway in the heart wall at the location in which stent 12 will be implanted. Preferably, the passageway will be formed using a dilation mechanism, and more preferably an inflatable dilation mechanism. The inflatable dilation mechanism can be positioned in the heart wall in a deflated configuration and then inflated to thereby dilate the heart wall, thus forming the passageway. A preferred inflatable dilation mechanism for forming such a passageway includes a balloon catheter 70, such as the one shown in FIG. 6. The balloon catheter can be fed over the guidewire with a dilation balloon 71 in a deflated condition. Thus, the catheter carrying a deflated dilation balloon advances through the anterior and posterior walls of the coronary artery and into the wall surrounding the left ventricle. The catheter may be inserted until balloon 71 resides within the heart wall. Preferably, the balloon has a length corresponding to approximately the thickness of the heart wall, and more preferably greater than or equal to the thickness of the heart wall, as measured during insertion of the hollow needle with either the measuring devices described above or through the use of utlrasound or the like. If the length of the balloon is greater than the thickness of the heart wall, the balloon may be positioned such that the excess length extends into the ventricle. The diameter of the inflated balloon is chosen so as to approximate the dimensions of the stent, for example diameter and length, that is desired in the heart wall. To facilitate positioning of the catheter, and in particular the balloon, with respect to the heart wall, a visualization technique, such as ultrasound or fluoroscopy, for example, or a mechanical mechanism, such as a mechanical stop, which may be formed by the balloon itself as will be explained shortly, may be utilized.

Figure 6:
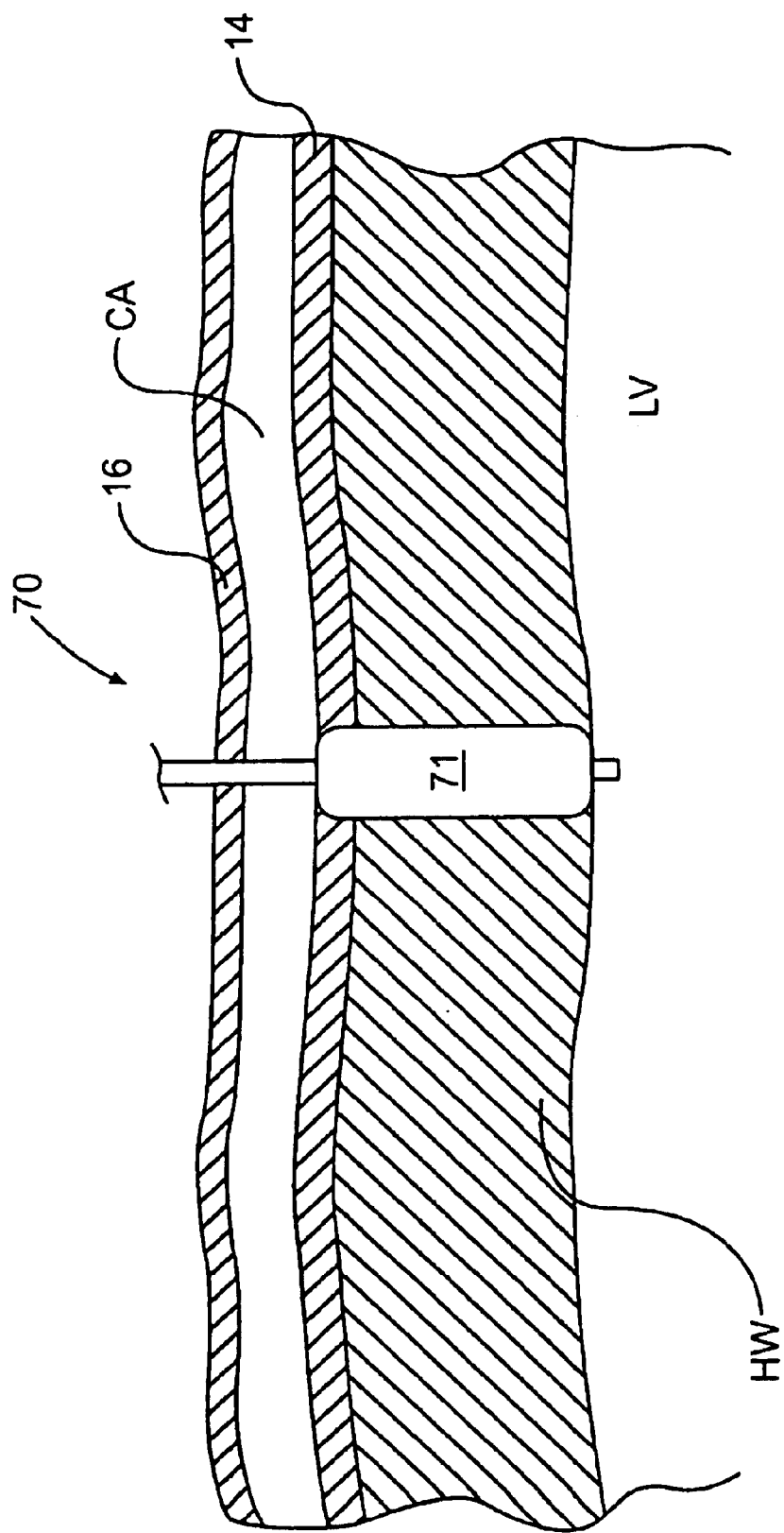
FIG. 6 is an embodiment of a catheter carrying a dilation balloon and placed, according to a method of the present invention, over the guidewire of FIG. 5 with the dilation balloon inflated to form a passageway in the heart wall between the left ventricle and coronary artery.

Once the catheter has been advanced such that dilation balloon 71 resides substantially within the heart wall, an inflation mechanism (not shown) is actuated to inflate the balloon. Balloon 71 is inflated as necessary to dilate the heart wall, causing a passageway to be formed therein, as shown in FIG. 6. The balloon preferably is made of a semi-compliant material to impart the appropriate dilation force to the heart wall. Preferably, the balloon will be inflated to a diameter corresponding to less than the maximum inflation extent of the balloon. This amount of inflation preferably will correspond to the desired dimensions, diameter and length, of the formed passageway. After dilating the heart wall and forming a passageway having desired dimensions, the balloon is deflated and removed from the passageway and the heart wall.

After removing the dilation balloon, the next step includes delivery of the stent into the as-formed passageway using a suitable delivery mechanism. In a preferred embodiment of this step, an inflatable delivery mechanism carrying the stent, such as a delivery balloon with stent 12 loaded thereon, is inserted into the passageway formed in the heart wall. Preferably, the balloon carrying the stent 12 is deflated and stent 12 is a collapsible stent that will be in a collapsed state when loaded onto the deflated delivery balloon. The stent 12 can be held in place on the delivery balloon by inflation pressure or other suitable mechanism.

Figure 7:
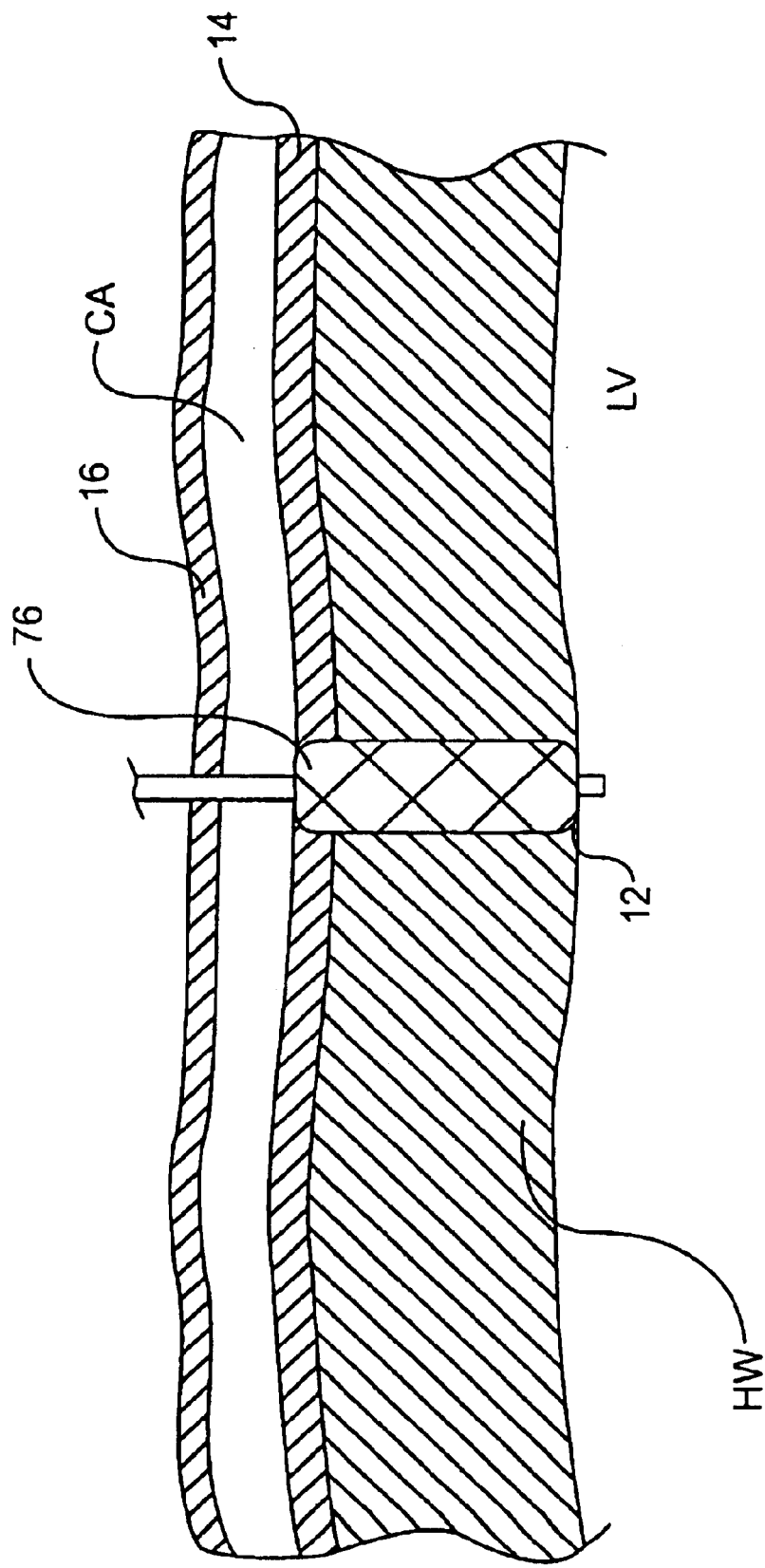
FIG. 7 is an embodiment of a catheter carrying a delivery balloon loaded with a stent, with the delivery balloon inflated to expand the stent and deliver the stent to the heart wall between the left ventricle and coronary artery, according to an embodiment of a method of the present invention.

As with dilation balloon 71, delivery balloon 76 (shown in FIG. 7) also will be carried by a catheter inserted over the guidewire. As will be explained shortly, the catheter carrying the delivery balloon can be either the same catheter or a different catheter than that carrying the dilation balloon. In either case, the catheter will be moved relative to the heart wall such that the stent-loaded delivery balloon is positioned within the formed passageway in the heart wall. Again, visualization techniques, such as ultrasound or fluoroscopy, for example, or a mechanical mechanism, such as a stop, for example, may be utilized in order to facilitate accurate placement of the delivery balloon, and thus stent 12, within the passageway. After the delivery balloon has been accurately positioned within the passageway, an inflation mechanism, which may be the same or different inflation mechanism used for the inflation of the dilation balloon, is actuated to inflate the delivery balloon. Upon inflation of the delivery balloon, stent 12 is expanded from its collapsed configuration. Preferably, the delivery balloon will be inflated to an extent that allows stent 12 to be fully expanded to fill the passageway created by the dilation balloon, and the inflated dimensions of the delivery balloon correspond to the full expansion of stent 12. FIG. 7 shows the delivery balloon inflated to expand stent 12 so that it fills the passageway in the heart wall.

Figure 8:
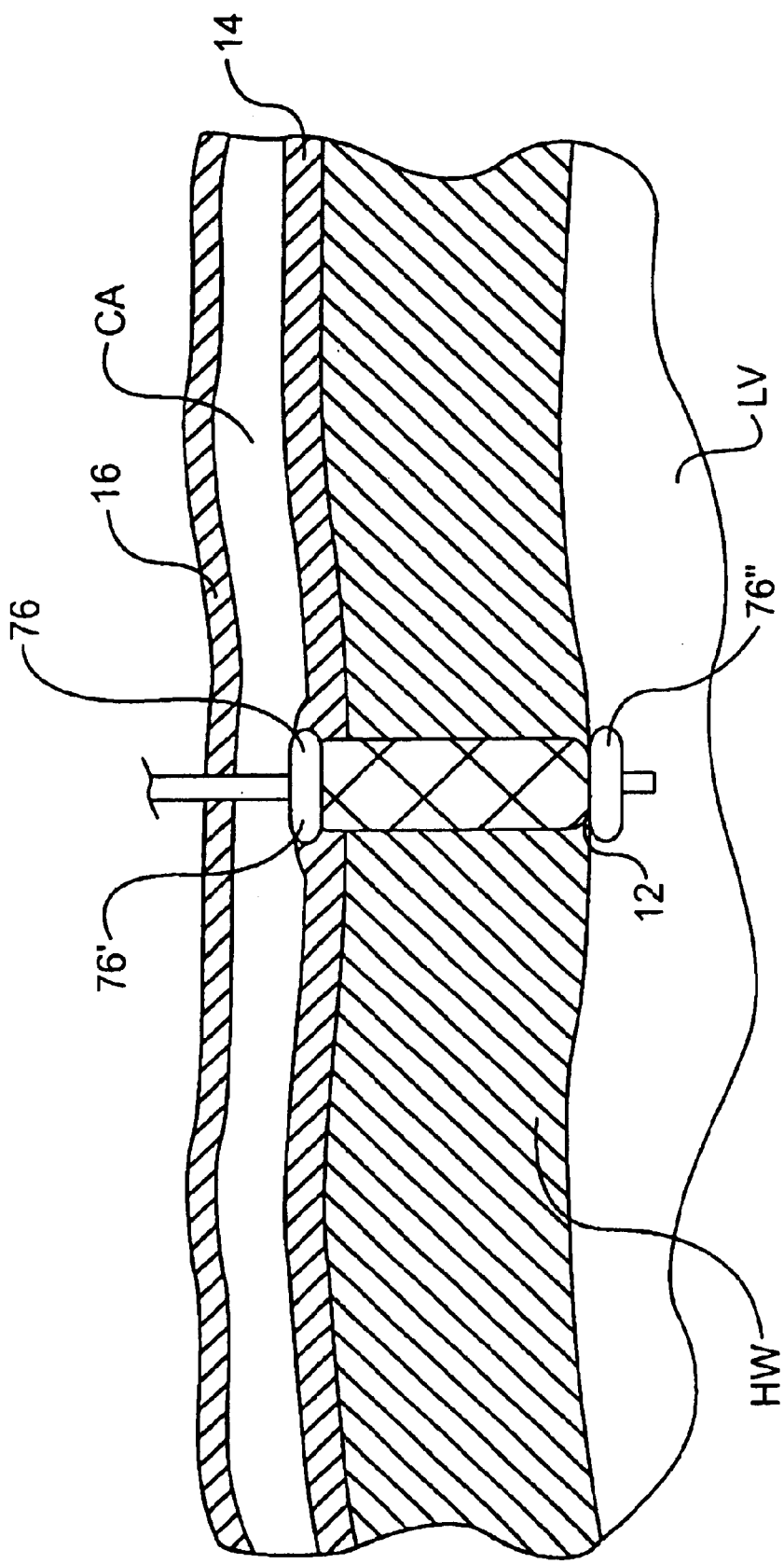
FIG. 8 is another embodiment of a catheter carrying a delivery balloon loaded with a stent, with the delivery balloon extending past the ends of the stent so as to form mechanical stops upon inflation of the delivery balloon, according to a method of the present invention.

In an embodiment of the invention, the length of delivery balloon 76 exceeds the length of stent 12 while collapsed. Stent 12 may be loaded onto the delivery balloon such that the deflated delivery balloon extends beyond each end of stent 12, and preferably at least from the proximal end of stent 12. As a result of extending beyond both ends of the stent, the balloon can expand during deployment beyond the ends of stent 12 and attain a dumbbell-like shape. In this manner, as illustrated for example in FIG. 8, by manipulation of the catheter, the proximal end 76' of the inflated balloon can provide a mechanical stop against the posterior wall of the coronary artery so that the proximal end of stent 12 can be positioned within the passageway to lie substantially flush with the posterior wall. If the ballon also extends beyond the distal end of stent 12, the distal end 76" of the inflated balloon also can provide a mechanical stop against the heart wall so that the distal end of stent 12 can be positioned within the passageway to lie substantially flush with the heart wall. Positioning of stent 12 substantially flush with the posterior wall of the coronary artery and the heart wall is preferable, according to one embodiment of the present invention, as was explained above to reduce the amount of stasis that occurs along the blood flow path from the left ventricle to the coronary artery and to reduce the risk of hematoma formation between the stent and the posterior artery wall.

Other embodiments of the inventive method include using a sheath as a dilation mechanism to form the passageway in the heart wall and to deliver the catheter carrying the stent to the heart wall. In embodiments using a sheath, after positioning the guide device in the desired location in the heart wall, a sheath may be advanced over the guidewire and inserted through the coronary artery and heart wall. The sheath will dilate the heart wall to form the passageway. Graduated markings may be placed on the outside of the sheath to determine the depth of penetration in the heart wall. A stent to be delivered may be preloaded on a balloon catheter and inserted over the guidewire and through the sheath to the appropriate position in the heart wall.

Figure 11:
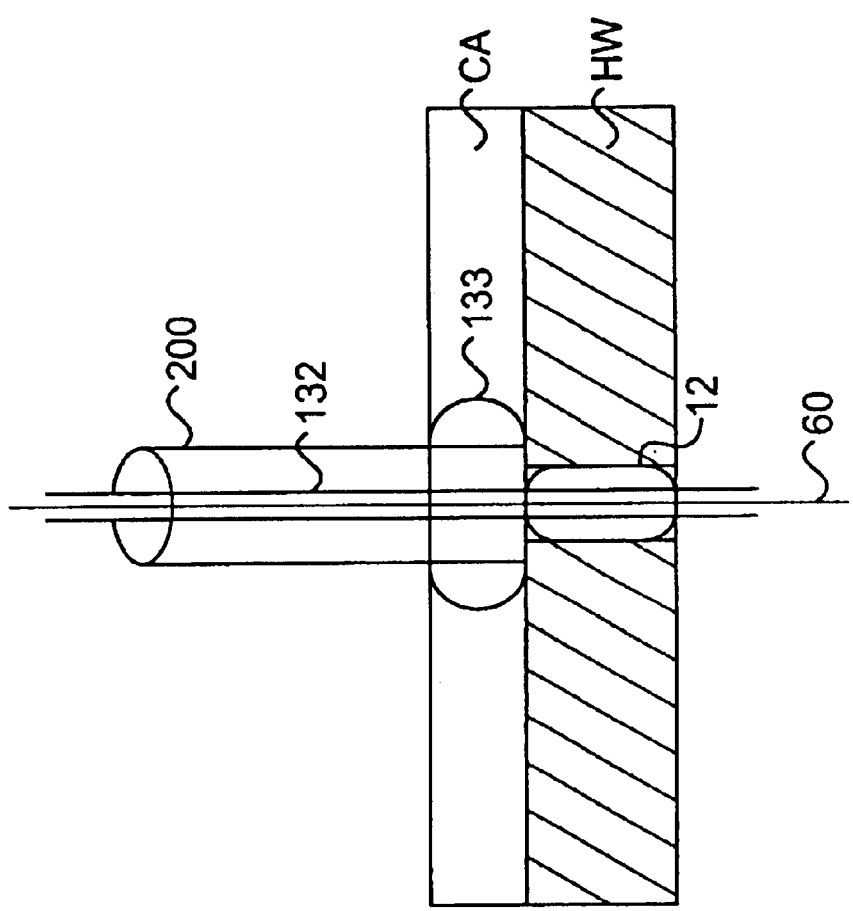
FIG. 11 is an embodiment of a sheath having a mechanical stop on a distal end used to deliver a balloon catheter carrying a stent, according to a method of the present invention.
Figure 12:
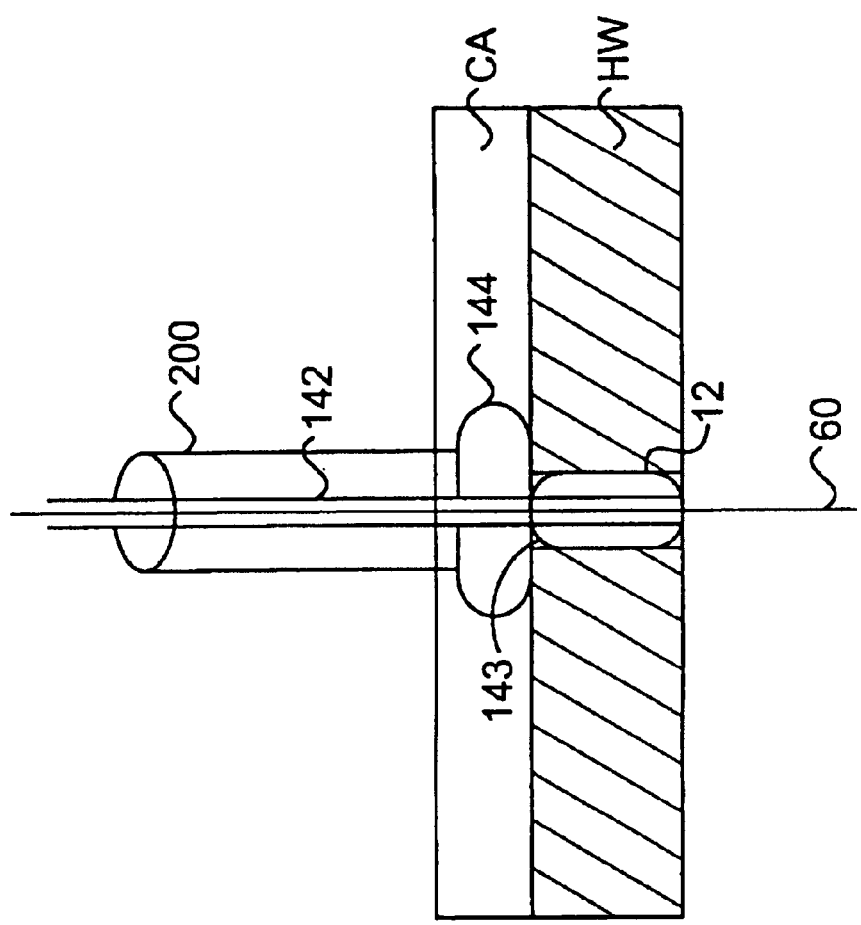
FIG. 12 is an embodiment of a sheath and a double balloon catheter having a proximal balloon configured to inflate substantially horizontally within the coronary artery to form a mechanical stop for stent delivery according to a method of the present invention.
Figure 13:
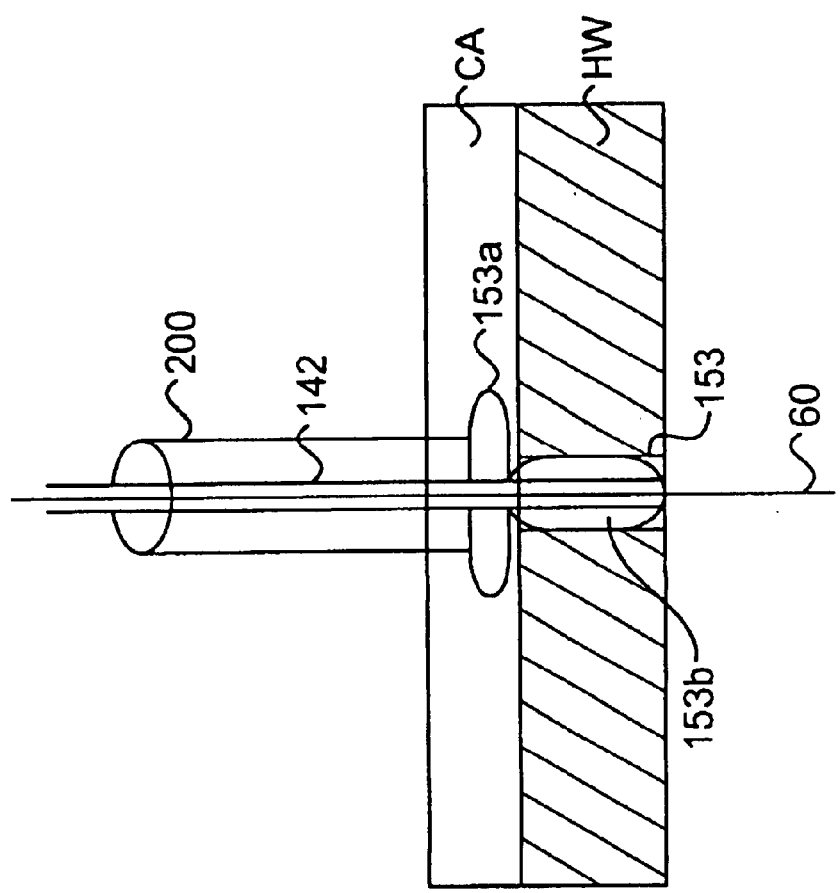
FIG. 13 is an embodiment of a sheath and balloon catheter with a T-shaped delivery balloon for stent delivery according to a method of the present invention.

In conjunction with this sheath delivery technique described above, various mechanisms, as shown for example in FIGS. 11–13, either alone or in combination, may be employed to facilitate appropriate positioning of the catheter and the stent with respect to the heart wall. In these embodiments of the invention, once the sheath has been inserted in the heart wall to dilate the heart wall and form the passageway, the sheath can then be retracted from the heart wall until a distal tip of the sheath resides within the coronary artery. Referring to FIG. 11, the distal tip of a sheath 200 may include a stop mechanism, such as, for example, an expandable basket 133 surrounding the distal opening of the sheath 200. Preferably, basket 133 is self-expanding, such as a nitinol basket for example, and has a diameter ranging from approximately 2 mm to approximately 3 mm. The basket 133 positions the distal tip of the sheath 200 in the coronary artery and fixes this position by engaging with either the posterior or anterior walls of the coronary artery to prevent sheath 200 from passing therethrough. Once the sheath 200 is positioned, the stent may be delivered to the heart wall by placing stent 12 just distal to the tip of sheath 200. The distance between the distal tip of sheath 200, positioned at the inner surface of the posterior wall of the coronary artery, and the top of stent 12 may be determined by graduated markings on a portion of a balloon catheter 132 carrying stent 12 and extending outside sheath 200.

After appropriate positioning of stent 12, a locking mechanism (not shown) on sheath 200 may be used to fix the position of catheter 132. Once stent 12 has been placed within the heart wall, sheath 200 and catheter 132 may be removed from the heart. To remove sheath 200, basket 133 first must be retracted or compressed.

FIG. 12 illustrates another mechanism which may be employed to facilitate the positioning of stent 12 within the heart wall. In this embodiment, after sheath 200 is inserted into the coronary artery, a double balloon catheter 142 is inserted over guidewire 60 and through sheath 200. Double balloon catheter 142 includes a distal balloon 143 carrying stent 12 and a smaller proximal balloon 144 that serves as a mechanical stop mechanism. Proximal balloon 144 preferably has a diameter ranging from approximately 2 mm to approximately 3 mm. Once balloon catheter 142 is inserted such that proximal balloon 144 is past the distal tip of sheath 200, proximal balloon 144 may be inflated. This inflation causes proximal balloon 144 to expand substantially in a horizontal direction past the distal opening of the sheath and to engage the anterior and posterior walls of the coronary artery. This holds the balloon catheter 142 in an appropriate position to place stent 12 within the heart wall. Distal balloon 143 can then be inflated to deliver stent 12. By positioning the distal end of proximal balloon 144 adjacent the posterior coronary artery wall and knowing the distance between the distal end of proximal balloon 144 and the proximal end of stent 12 on distal balloon 143, the depth of insertion within the heart wall may be determined.

FIG. 13 depicts the use of a T-shaped balloon in conjunction with a sheath delivery technique to assist in accurate positioning of stent 12 in the heart wall. In this embodiment, a balloon catheter 152 has a single T-shaped balloon 153, with stent 12 being carried by the lower, vertically-extending portion of the balloon 153. Sheath 200 is inserted, as described above, until the distal tip reaches the interior of the coronary artery. Balloon catheter 152 carrying stent 12 then is inserted through sheath 200 and over guidewire 60 until the upper, horizontally-extending portion 153a of balloon 153 is past the distal tip of sheath 200 and is within the coronary artery. Inflating balloon 153 at this point creates a mechanical stop mechanism similar to small proximal balloon 144 discussed above. That is, the upper, horizontally-extending portion 153a of T-shaped balloon 153 engages with at least the posterior wall of the coronary artery to appropriately position the lower, vertically-extending portion 153b of balloon 153, and thus stent 12, within the heart wall. Once stent 12 has been delivered and placed within the heart wall, balloon 153 can be deflated and catheter 152 and sheath 200 removed.

Regardless of the delivery technique employed, stent 12 preferably will be selected such that, upon full expansion, the conduit will have dimensions that cause the passageway in the heart wall to remain open, thereby creating a permanent passageway between the left ventricle and the coronary artery. Moreover, stent 12 preferably will have a length that approximately equals or is greater than the thickness of the heart wall. More preferably, the length of stent 12 is large enough to allow a small end portion of stent 12 to reside in the left ventricular chamber in order to prevent invagination of the tissue around the opening of the stent. Even more preferably, the length of the stent may be chosen such that it covers the systolic depth of the heart wall measured from the posterior wall of the coronary artery to the inner surface of the left ventricular wall. This systolic depth may be determined using visualization techniques, such as echocardiography, for example. In any case, the length of the stent 12 to be used may be determined from the measurements of the heart wall determined previously, for example using the hollow needle, in combination with the determination of the coronary artery diameter using appropriate visualization techniques.

In addition, the stent preferably will be made of or coated internally with a material that prevents heart wall tissue, blood, and debris from prolapsing into the stent. Such a material may include a woven or a non-woven polymer that is compatible with blood and has low thrombogenicity, or other coatings to improve resistance to thrombus formation or tissue overgrowth. Coatings that enhance endothelial cell formation also are desired. Moreover, the stent may include a drug delivery coating. Other materials exhibiting these characteristics while also allowing deployment by the inventive method also are within the scope of the invention.

A further preferable feature of the stent to be implanted in the heart wall includes a flow controller disposed within the stent. Such a flow controller preferably would bias flow in the net forward direction, i.e., in the direction flowing from the ventricle to the coronary artery. Flow control mechanisms of this type include autologous vein sections, xenograft vein or valve sections, tilting disks, ball-in-cage valves, tapered shunt configurations, lobed duckbill flaps, mechanical poppets, pressure or electrically activated valves, and other suitable like mechanisms. Examples of various flow control mechanisms used with stents to create a net forward flow from the left ventricle to the coronary artery can be found in commonly-owned U.S. patent application Ser. No. 09/368,393, filed Aug. 4, 1999, and entitled "Valve Designs for Left Ventricular Conduits." The entire disclosure of that application is incorporated by reference herein.

Figure 14:
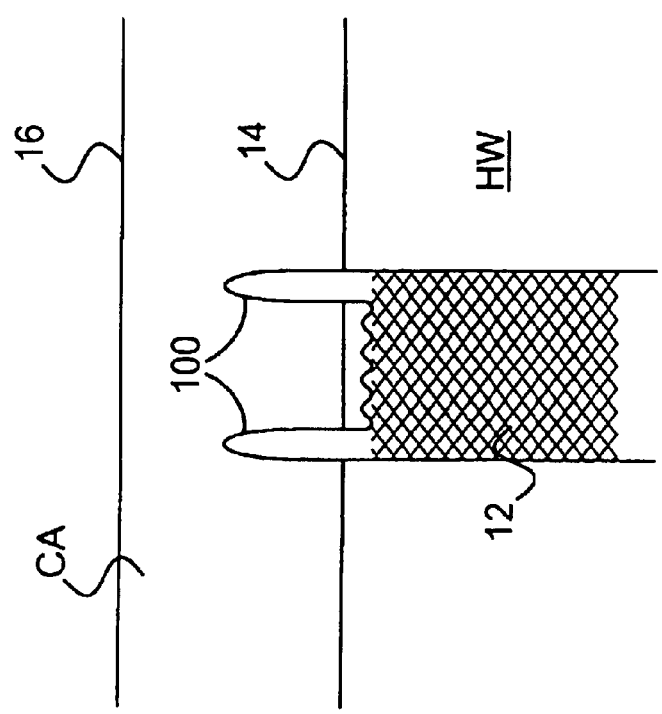
FIG. 14 is a stent having extensions at an end nearest the coronary artery, according to an embodiment of the present invention.

In another embodiment of a flow controller, a stent may be used to create a natural valving mechanism to reduce the potential occurrence of backflow of blood from the coronary artery to the left ventricle during portions of the cardiac cycle, particularly diastole. This will be described in connection with FIGS. 14, 15a, and 15b. To create a natural valving mechanism, stent 12 may include a pair of extensions, or struts 100, extending beyond the end of the stent nearest the posterior wall 14 of the coronary artery CA, as shown in FIG. 14. Struts 100 preferably are approximately 180° apart from each other and each strut 100 may have a length of approximately 0.5 mm to approximately 1 mm. Struts 100 may be formed by removing portions of a stent between the struts or by any other suitable manner known in the art. Additional struts, or different placements or lengths of the struts, may be used. The stent used for creating a valving mechanism may be with or without additional struts as needed to keep the oval-shaped opening shown in FIGS. 15a and 15b patent. In addition, the stent may be placed so that the portion of the stent (not including the struts) ends somewhat below the posterior wall 14 of the coronary artery CA, particularly during the diastolic phase of the cardiac cycle.

Figures 15A, 15B:
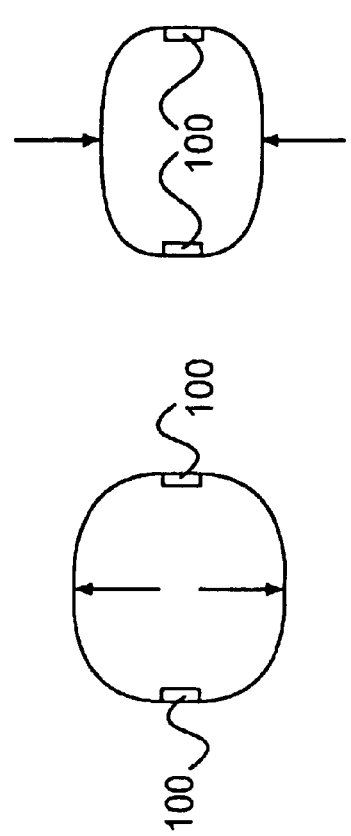
FIGS. 15a and 15b each is a myocardial passageway having the stent of FIG. 14, as seen from the coronary artery during systole and diastole, respectively.

This placement of the stent, along with the struts 100, causes natural valving to occur, as described with reference to FIGS. 15a and 15b. These Figures depict the passageway containing stent 12 in the heart wall, as viewed from the coronary artery looking into the passageway. FIG. 15a shows the circular shape of that passageway during systole, and the position of struts 100. The arrows in FIG. 15a depict the opening of the top of the passageway at the posterior wall of the coronary artery caused by the flow of blood from the left ventricle to the coronary artery. FIG. 15b shows an oval shape of the end of the passageway nearest the coronary artery during diastole. The posterior wall of the artery flattens out around struts 100 due to a drop in diastolic pressure as compared to normal conditions because of the placement of the stent 12. This causes the coronary artery to collapse during diastole, in turn causing the oval-shaped opening of the end of the stent disposed nearest the coronary artery as shown by the arrows in FIG. 15b. Thus, the depth of stent 12 being somewhat below the posterior wall of the coronary artery, in combination with struts 100 extending into the coronary artery, permits that posterior wall to at least partially close the passageway in the heart wall during diastole, restricting flow of blood back into the left ventricle from the coronary artery. In contrast, relatively rapid and extensive pressure rise during systole occurs due to increasing flow from the ventricular side. This causes the opening of the passage nearest the coronary artery to open to the position shown in FIG. 15a. It may also be preferable in certain embodiments to include a natural valve mechanism, like that shown in FIGS. 14–15b, at the end of the stent nearest the left ventricle.

Once stent 12 has been expanded and positioned in the passageway in the heart wall, the delivery balloon is deflated. The catheter carrying the delivery balloon can then be removed from the patient by sliding it over the guidewire. The guidewire also can be removed from the patient and the puncture site in the artery can be closed via conventional suturing methods and/or surgical sealants, or other suitable closure techniques and mechanisms. In certain embodiments, a closing device similar to those used and known to close a patent foramen ovale may be used. Also, the inner part of the closing device which covers the inner surface of the coronary artery may be constructed without any Dacron or covering material as long as the fixation of the closing device is maintained by suitable fixation members. An outer portion of the closing device, made for example of a biocompatible covering material like Dacron, may then be connected to the inner portion of the closing device to close the hole.

Alternatively, it may be possible to close the hole in the anterior wall of the artery by retracting the wall of the artery without any closing device. Such a technique would be similar to using a suture, but would not require assistance by the surgeon. For example, as the hole in the artery is formed by introducing a sheath over a wire, the tissue surrounding the hole is compressed around the sheath. After removing the sheath, this tissue will tend to cause a portion of the artery wall to retract to close the hole. To assist in this process, a small outer ring may be fixed to the outside surface of the artery. This outer ring may be formed of a suitable closure material, such as a suture or glue. The ring may be applied prior to removing the sheath, essentially using the outer surface of the sheath as an applicator. Once the ring is fixed to the outer surface of the coronary artery, the sheath may be removed. The ring may then retract the tissue surrounding the hole to close the hole in the coronary artery.

As discussed above, the steps of dilating the heart wall using a balloon catheter to form the passageway and implanting the conduit can be performed by using separate catheters for each step, a first catheter carrying the dilation balloon and a second catheter carrying the delivery balloon and stent. As an alternative, a single catheter carrying both a delivery balloon and a dilation balloon and stent in a collinear manner may be used. If two separate catheters are employed, one carrying the dilation balloon and one carrying the delivery balloon, a catheter exchange technique is employed. That is, after the catheter carrying the dilation balloon has been employed to form the passageway in the heart wall, the dilation balloon will be deflated and the catheter will be slid along the guidewire and removed from the patient. Then, the catheter carrying the delivery balloon with the collapsed stent loaded thereon is inserted over the guidewire and into the correct position with respect to the heart wall, and the conduit is implanted as described above.

Figure 3:
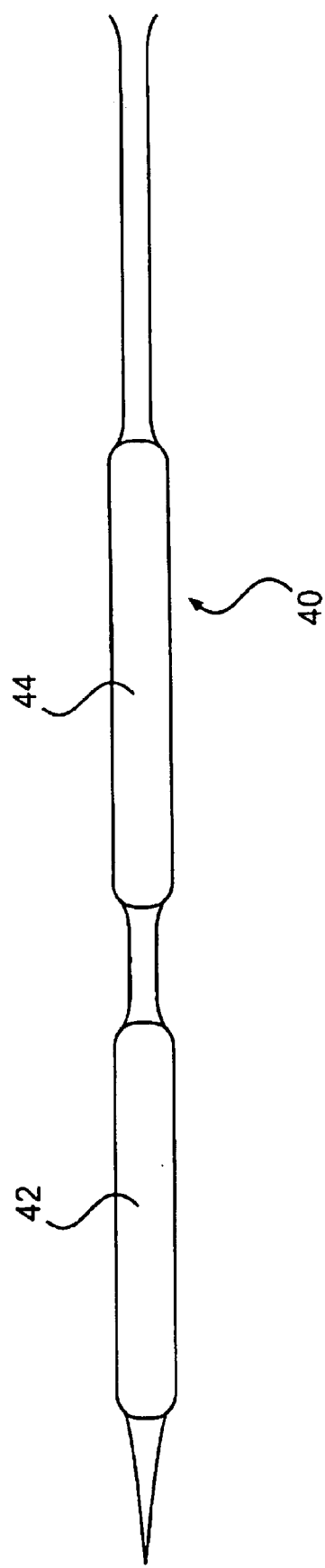
FIG. 3 is an embodiment of a double-balloon catheter for use in a method according to an embodiment of the present invention.
Figure 9:
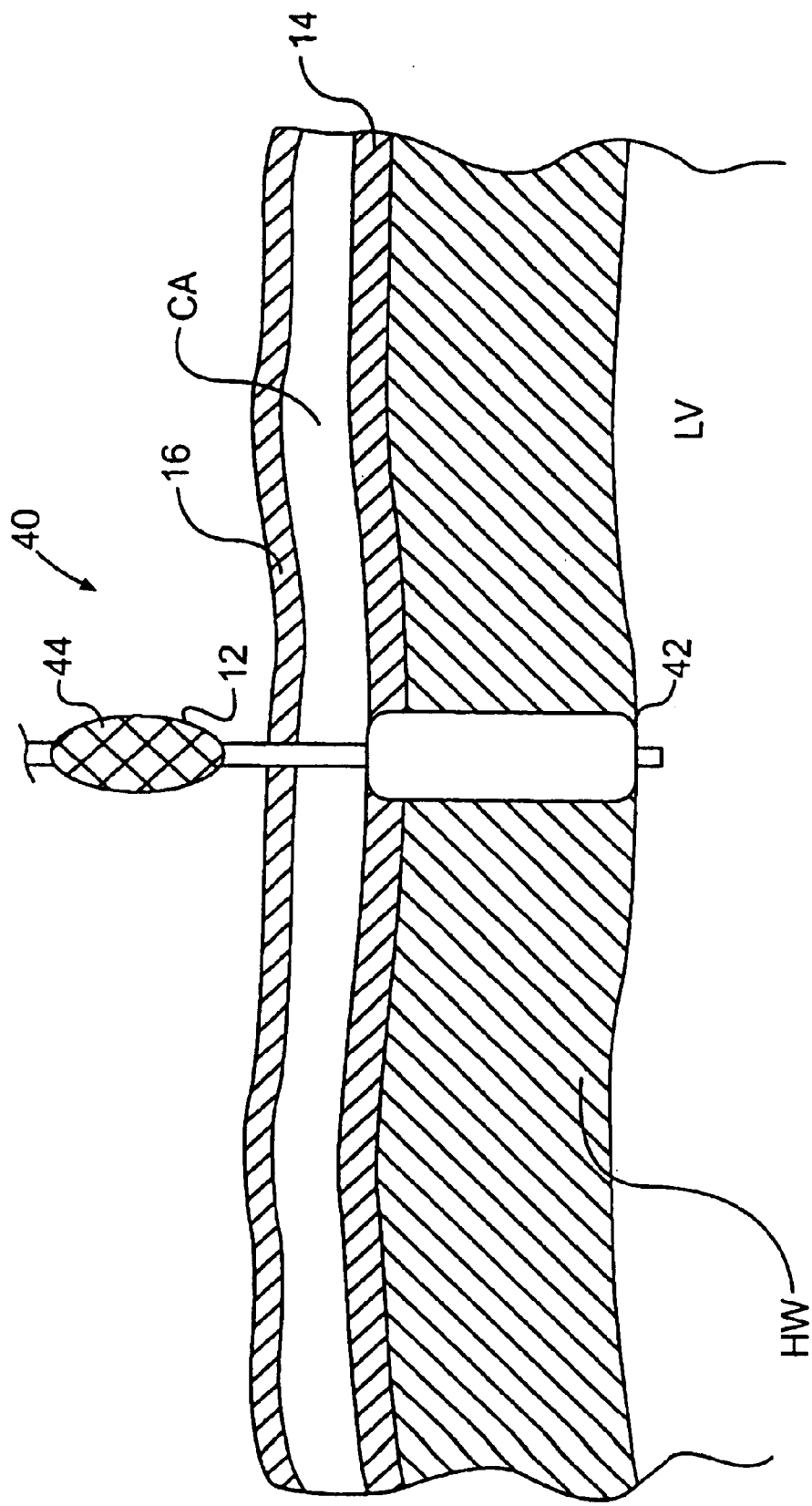
FIG. 9 is an embodiment of a double balloon catheter of the type of FIG. 3 shown with the dilation balloon inflated to form a passageway in the heart wall between the left ventricle and coronary artery, according to an embodiment of a method of the present invention.
Figure 10:
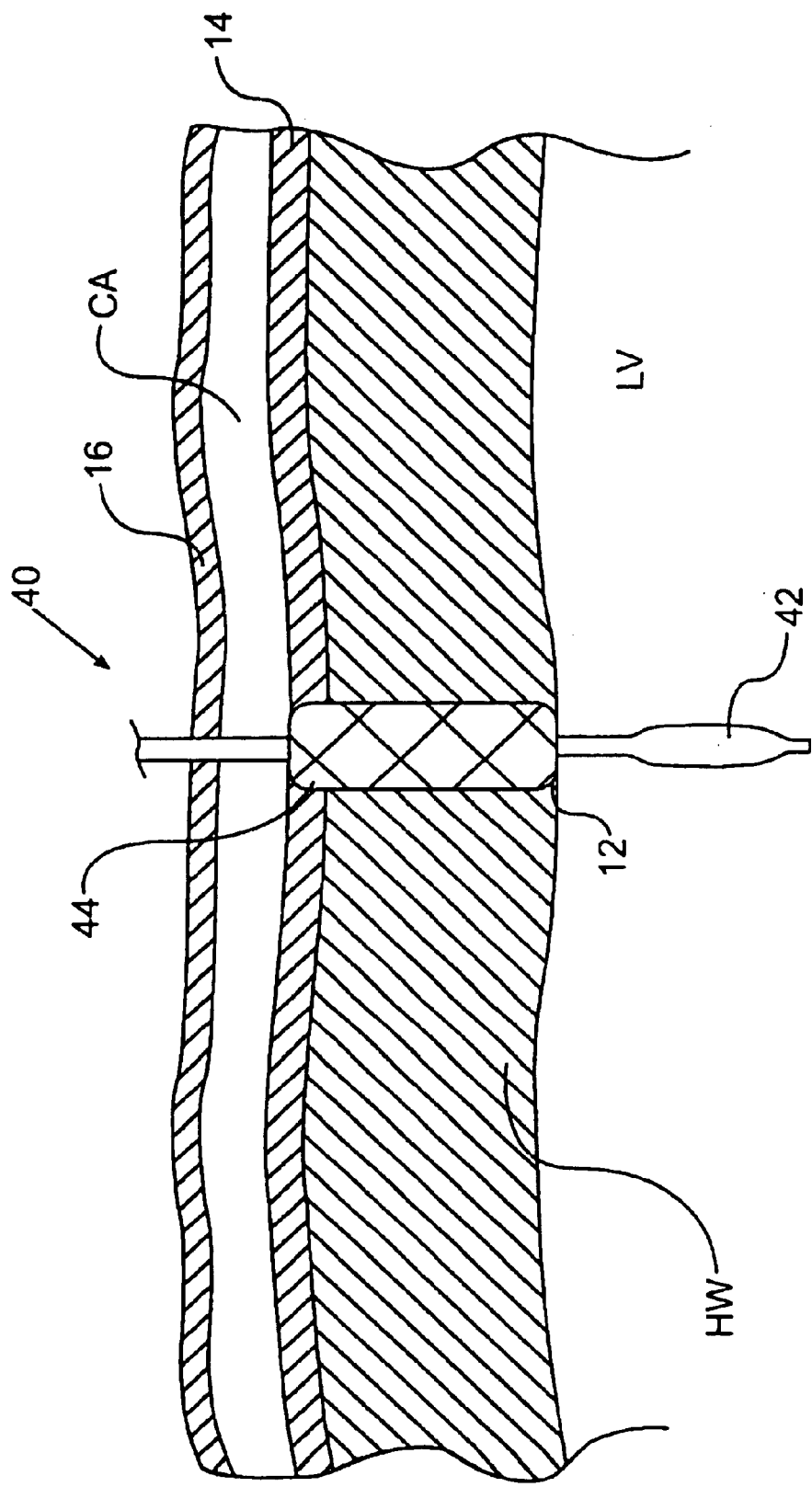
FIG. 10 is the embodiment of the double balloon catheter of FIG. 9 in an advanced position with the delivery balloon positioned in the heart wall and inflated to deliver the stent to the heart wall and the dilation balloon resting in the left ventricle in a deflated state, according to a method of the present invention.

If a single catheter carrying both the dilation and the delivery balloons is employed, the method is performed in the following manner. FIG. 3 shows an embodiment of such a catheter 40 having at least two colinear balloons, a first dilation balloon 42 at a distal end and a second delivery balloon 44 just proximal of dilation balloon 42. FIG. 3 shows just the distal end of catheter 40. Both balloons are connected to suitable inflation mechanisms known in the art. The same inflation mechanism can be used to inflate both balloons or two separate inflation mechanisms can be used. A suitable, exemplary length of each balloon is approximately 30 mm, and a suitable, exemplary diameter of each balloon is approximately 2.5–3.5 mm. The deflated delivery balloon 44 is loaded with the stent, not shown in FIG. 3. The catheter 40 is inserted over the guidewire and advanced until the dilation balloon 42 resides within the heart wall in the manner described above with reference to the discussion of the deployment of the dilation balloon to form the passageway. Once properly positioned within the heart wall, the dilation balloon 42 is inflated to form the passageway, as shown in FIG. 9. After the passageway has been formed, the dilation balloon 42 is deflated and the catheter is further advanced until the delivery balloon 44 is positioned within the passageway, also as discussed above. In this position, the portion of the catheter 40 carrying the deflated dilation balloon 42 will come to a rest in the left ventricular chamber. To implant the stent in the passageway, the delivery balloon 44 is inflated, causing expansion of the stent to fill the passageway, as shown in FIG. 10. Once the stent expands so as to be in contact with the heart wall surrounding the passageway, the delivery balloon 44 is deflated and the entire catheter 40 removed from the patient. The guidewire can be removed as well, leaving only the stent remaining to form a permanent passageway between the coronary artery and the left ventricle. The multiple balloon catheter shown in FIGS. 4, 9, and 10 may incorporate a delivery balloon of the type shown in FIG. 8.

In one aspect of the invention, the method includes using a multiple balloon stent delivery catheter of the type shown in FIG. 3 to perform the dilation of the heart wall to form the passageway and the implantation of the stent in a single insertion of the catheter over the guidewire, as just described. Suitable multiple balloon stent delivery catheters are disclosed in U.S. Pat. No. 4,763,654 issued to Jang and entitled "Tandem Independently Inflatable/Deflatable Multiple Diameter Balloon Angioplasty Catheter System and Method of Use" and U.S. Pat. No. 5,725,535 issued to Hedge et al. and entitled "Multiple Balloon Stent Delivery Catheter and Method." The complete disclosures of these patents are incorporated by reference herein. The disclosed catheters include a distal balloon and inner and outer concentric balloons located proximal the distal balloon. In the method according to the present invention, the distal balloon is used to form the passageway by dilating the heart wall. The stent in a collapsed configuration can be loaded onto the outer concentric balloon, and the concentric balloons can be used to deliver the stent into the passageway by inflating either one of the inner and outer balloons or both the inner and outer balloons consecutively. In this catheter, the outer balloon is configured to expand to a greater extent than the inner balloon. However, the inner balloon may be configured to expand a to an extent large enough that allows the outer balloon, and thus the stent, to expand such that the stent fits the passageway formed by the distal, dilation balloon. The outer concentric balloon can optionally be inflated to further expand the stent and the passageway formed by the distal, delivery balloon if such expansion is needed.

Other embodiments of the invention will be apparent to those skilled in the art from consideration of the specification and practice of the invention disclosed herein. The specification and examples are exemplary only, with a true scope and spirit of the invention being indicated by the following claims.

What is claimed is:

1. A method of treating a heart, the method comprising the steps of:

placing a guidewire through an anterior wall and a posterior wall of a coronary vessel and through a heart wall between a heart chamber and the coronary vessel;

advancing catheter carrying a stent along the guidewire through the anterior wall and the posterior wall of the coronary vessel and into the heart wall; and expanding the stent within the heart wall.

2. The method of claim 1, further comprising forming a passageway in the heart wall at a location defined by the guidewire.

3. The method of claim 2, wherein forming the passageway includes providing a dilation mechanism at the location defined by the guidewire.

4. The method of claim 3, wherein the dilation mechanism includes a sheath.

5. The method of claim 3, wherein forming the passageway further includes expanding the dilation mechanism.

6. The method of claim 5, wherein the expanding the dilation mechanism includes inflating the dilation mechanism.

7. The method of claim 2, further comprising delivering via the guidewire a first mechanism for forming the passageway in the heart wall and a second mechanism for placing the stent within the passageway.

8. The method of claim 7, wherein the first and second mechanisms are delivered via the guidewire to the heart simultaneously.

9. The method of claim 7, wherein the first mechanism is delivered via the guidewire to the heart and, after the first mechanism is removed from the heart via the guidewire, the second mechanism is delivered via the guidewire to the heart.

10. The method of claim 7, wherein the second mechanism includes a stop mechanism and wherein the method further comprises advancing the stent within the passageway until the stop mechanism engages one of a wall of the coronary vessel and a surface of the heart wall.

11. The method of claim 10, wherein the stent is advanced until the stop mechanism engages the posterior wall of the coronary vessel.

12. The method of claim 11, wherein the stop mechanism is located at substantially a proximal end of the stent during the delivery of the stent.

13. The method of claim 7, wherein the first mechanism includes a stop mechanism and delivering the first mechanism includes engaging the stop mechanism with at least one inner wall of the coronary vessel.

14. The method of claim 13, wherein engaging the stop mechanism includes expanding the stop mechanism.

15. The method of claim 2, wherein forming the passageway includes inserting a sheath into the location defined by the guidewire.

16. The method of claim 2, wherein forming the passageway includes inserting a balloon into the location defined by the guidewire and inflating the balloon.

17. The method of claim 16, wherein inserting the balloon includes inserting a catheter carrying the balloon over the guidewire.

18. The method of claim 16, further comprising deflating the balloon after forming the passageway, and removing the balloon from the passageway after deflating the balloon.

19. The method of claim 2, wherein the passageway is formed and the stent is delivered by the catheter carrying a first expansion device and a second expansion device.

20. The method of claim 19, wherein the first and second expansion devices include inflation devices.

21. The method of claim 20, wherein the first inflation device is a first balloon and the second inflation device is a second balloon.

22. The method of claim 21, further comprising inserting the catheter over the guidewire so that the first balloon is positioned in the location.

23. The method of claim 22, further comprising inflating the first balloon to form the passageway.

24. The method of claim 23, further comprising deflating the first balloon after forming the passageway, and further inserting the catheter over the guidewire so that the second balloon is positioned in the passageway.

25. The method of claim 24, wherein the second balloon carries the stent, and further comprising inflating the second balloon to place the stent within the passageway.

26. The method of claim 22, wherein the second balloon is positioned within the coronary vessel when the first balloon is positioned at the location.

27. The method of claim 26, further comprising inflating the second balloon so that the second balloon engages at least one interior wall of the coronary vessel and inflating the first balloon, the first balloon carrying the stent.

28. The method of claim 2, wherein the step of forming the passageway is prior to the step of advancing the stent.

29. The method of claim 2, wherein the step of forming the passageway is prior to the step of expanding the stent.

30. The method of claim 2, wherein expanding the stent includes expanding the stent in the passageway.

31. The method of claim 2, wherein advancing the stent includes placing the stent in the passageway.

32. The method of claim 1, wherein the stent is a collapsible stent.

33. The method of claim 1, further comprising measuring a distance from the anterior wall of the coronary vessel to the heart chamber prior to placing the guide device.

34. The method of claim 1, further comprising the step of inserting a hollow needle through the anterior wall and the posterior wall of the coronary vessel and the heart wall, prior to placing the guidewire.

35. The method of claim 34, wherein the step of placing the guidewire includes inserting the guidewire through the hollow needle until an end of the guidewire rests in the heart chamber.

36. The method of claim 35, further comprising the step of removing the hollow needle after inserting the guidewire through the hollow needle.

37. The method of claim 34, further comprising the step of measuring a depth of insertion of the hollow needle.

38. The method of claim 37, wherein the measuring step includes viewing markings on the hollow needle, the markings indicating the depth of insertion of the hollow needle.

39. The method of claim 38, further comprising determining the thickness of the heart wall by subtracting a diameter of the coronary vessel from the distance measured by the needle, and selecting said stent based on the heart wall thickness.

40. The method of claim 34, further comprising avoiding intracardiac structures during insertion of the hollow needle.

41. The method of claim 1, further comprising placing the guidewire at a predetermined angle relative to the posterior wall of the coronary vessel.

42. The method of claim 41, wherein placing the guidewire at a predetermined angle includes inserting a hollow needle at the predetermined angle through the anterior wall and the posterior wall of the coronary vessel and the heart wall, prior to placing the guidewire.

43. The method of claim 1, wherein expanding the stent includes expanding the stent with an expansion device.

44. The method of claim 43, wherein the expansion device includes an inflation device.

45. The method of claim 44, wherein the inflation device is a balloon that carries the stent, and expanding the stent includes inserting the balloon and the stent within the heart wall and inflating the balloon.

46. The method of claim 43, wherein inserting the balloon and the stent includes inserting the catheter carrying the balloon and the stent over the guidewire.

47. The method of claim 1, further comprising advancing the stent within the heart wall until a stop mechanism engages the posterior wall of the coronary vessel.

48. The method of claim 47, wherein the stop mechanism is provided proximate a proximal end of the stent.

49. The method of claim 1, further comprising engaging a stop mechanism with at least one interior wall of the coronary vessel.

50. The method of claim 1, further comprising placing the stent in the heart wall so as to permit blood to flow between the heart chamber and the coronary vessel via the stent.

51. The method of claim 50, wherein the heart chamber is a left ventricle.

52. The method of claim 51, wherein the coronary vessel is a coronary artery.

53. A method of treating a heart, the method comprising:
inserting a needle through an anterior wall and a posterior wall of a coronary vessel;
after inserting the needle, piecing a guidewire through the needle past the anterior wall and the posterior wall of the coronary vessel and through a heart wall between a heart chamber and the coronary vessel;
inserting an expansion device along the guidewire through the anterior wall and the posterior wall of the coronary vessel and into the heart wall;
expanding the expansion device within the heart wall to form a passageway between the heart chamber and the coronary vessel; and
placing a stent within the passageway.

54. The method of claim 53, wherein the stent is collapsible and placing the stent within the passageway includes delivering the stent to the passageway in a collapsed configuration and then expanding the stent within the passageway.

55. The method of claim 54, wherein delivering the stent includes providing an inflatable delivery mechanism onto which the stent is loaded and expanding the stent includes inflating the delivery mechanism.

56. The method of claim 53, wherein the expansion device includes a first expandable mechanism and a second expandable mechanism, and expanding the first expandable mechanism forms the passageway and expanding the second expandable mechanism places the stent within the passageway.

57. The method of claim 56, wherein the first and second expandable mechanisms are inflatable mechanisms and the expanding the first and second expandable mechanisms includes inflating the first and second expandable mechanisms.

58. The method of claim 53, further comprising determining the thickness of the heart wall prior to inserting the expansion device, wherein the stent is selected based on the thickness of the heart wall.

59. The method of claim 53, wherein the step of placing the guidewire includes placing the guidewire through the hollow needle until an end of the guidewire rests in the heart chamber.

60. The method of claim 59, further comprising the step of removing the hollow needle after inserting the guidewire through the hollow needle.

61. The method of claim 53, further comprising the step of measuring a depth of insertion of the hollow needle.

62. The method of claim 53, further comprising avoiding intracardiac structures during insertion of the hollow needle.

63. The method of claim 53, wherein the expansion device is a balloon catheter and inserting the expansion device includes advancing the catheter over the guidewire until a distal balloon at a distal end of the balloon catheter is within the heart wall.

64. The method of claim 63, wherein the balloon catheter includes the distal balloon and a proximal balloon, and inflating the distal balloon forms the passageway and inflating the proximal balloon places the stent within the passageway.

65. The method of claim 64, further comprising, after forming the passageway, deflating the distal balloon and advancing the balloon catheter so that the distal balloon rests in the left ventricle and the proximal balloon is in the passageway.

66. The method of claim 64, wherein the stent is loaded on the proximal balloon in a collapsed configuration and inflating the proximal balloon expands the stent and places the stent within the passageway.

67. The method of claim 63, wherein the stent is placed by a second catheter carrying a second expansion device.

68. The method of claim 67, wherein the second expansion device is a balloon and the balloon is inflated to place the stent.

69. The method of claim 67, wherein the balloon catheter is removed after the passageway is formed and then the second catheter is inserted into the formed passageway to place the stent.

70. The method of claim 53, wherein inserting the expansion device includes inserting the expansion device over the guidewire extending between the heart wall and exterior the heart chamber and the coronary vessel.

71. The method of claim 53, further comprising placing the stent in the heart wall so as to permit blood to flow between the heart chamber and the coronary vessel via the stent.

72. The method of claim 71, wherein the heart chamber is a left ventricle.

73. The method of claim 72, wherein the coronary vessel is a coronary artery.

74. A method of treating a heart, the method comprising the steps of:
    inserting a needle through an anterior wall and a posterior wall of a coronary vessel;
    after inserting the needle, placing a guidewire through the needle pas the anterior wall and posterior wall of the coronary vessel and through a heart wall between a heart chamber and the coronary vessel;
    advancing a stent along the guidewire through the anterior wall and the posterior wall of the coronary vessel and into the heart wall; and
    expanding the stent within the heart wall.

* * * * *

UNITED STATES PATENT AND TRADEMARK OFFICE
CERTIFICATE OF CORRECTION

PATENT NO.     : 6,854,467 B2
DATED          : February 15, 2005
INVENTOR(S)    : Peter Boekstegers It is certified that error appears in the above-identified patent and that said Letters Patent is hereby corrected as shown below:

Column 16,
Line 21, "claim 43," should read -- claim 45, --.
Line 42, "piecing" should read -- placing --.

Column 18,
Line 29, "pas" should read -- past --.

Signed and Sealed this

Thirty-first Day of May, 2005

JON W. DUDAS
*Director of the United States Patent and Trademark Office*

UNITED STATES PATENT AND TRADEMARK OFFICE
CERTIFICATE OF CORRECTION

PATENT NO. : 6,854,467 B2
DATED : February 15, 2005
INVENTOR(S) : Peter Boekstegers It is certified that error appears in the above-identified patent and that said Letters Patent is hereby corrected as shown below:

<u>Column 14,</u>
Line 19, "advancing catheter," should read -- advancing a catheter, --.

Signed and Sealed this

Twentieth Day of September, 2005

JON W. DUDAS
*Director of the United States Patent and Trademark Office*